(12) United States Patent
Hockenberry et al.

(10) Patent No.: US 7,241,804 B1
(45) Date of Patent: Jul. 10, 2007

(54) COMPOSITIONS AND METHODS FOR MODULATING APOPTOSIS IN CELLS OVER-EXPRESSING BCL-2 FAMILY MEMBER PROTEINS

(75) Inventors: David M. Hockenberry, Seattle, WA (US); Julian A. Simon, Seattle, WA (US); Shie-Pon Tzung, Issaquah, WA (US)

(73) Assignee: Fred Hutchinson Cancer Research Center, Seattle, WA (US)

(*) Notice: Subject to any disclaimer, the term of this patent is extended or adjusted under 35 U.S.C. 154(b) by 675 days.

(21) Appl. No.: 10/069,431

(22) PCT Filed: Aug. 18, 2000

(86) PCT No.: PCT/US00/22891

§ 371 (c)(1),
(2), (4) Date: Jul. 30, 2002

(87) PCT Pub. No.: WO01/14365

PCT Pub. Date: Mar. 1, 2001

(51) Int. Cl.
*A61K 31/35* (2006.01)
(52) U.S. Cl. ...................... 514/450; 549/267
(58) Field of Classification Search ................ 514/450; 549/267
See application file for complete search history.

(56) References Cited

U.S. PATENT DOCUMENTS

| 5,641,866 | A |  | 6/1997 | Reed et al. |
| 5,643,727 | A |  | 7/1997 | Reed et al. |
| 5,659,024 | A |  | 8/1997 | Reed et al. |
| 5,686,595 | A |  | 11/1997 | Reed et al. |
| 5,702,897 | A |  | 12/1997 | Reed et al. |
| 5,734,033 | A |  | 3/1998 | Reed |
| 5,744,310 | A |  | 4/1998 | Reed |
| 5,994,564 | A | * | 11/1999 | Van Sickle ............. 549/267 |
| 5,998,583 | A |  | 12/1999 | Korsmeyer |
| 6,355,660 | B1 | * | 3/2002 | Ricks et al. ............ 514/357 |

FOREIGN PATENT DOCUMENTS

| EP | 1 054 011 | 11/2000 |
| JP | 7-196489 | 8/1995 |
| JP | 5-155877 | 6/2003 |
| WO | WO 99/40081 | 8/1999 |
| WO | WO 01/05769 | 1/2001 |

OTHER PUBLICATIONS

Huang, Bcl-2 family proteins as targets for anticancer drug design, Oncogene (2000) 19, 6627-6631.*
Tzung, Antimycin A mimics a cell-death-inducing Bcl-2 homology domain 3, Nature Cell Biology, vol. 3, (2001) 183-191.*
Tokuatke et al., "Inhibition Of Electron Transport Of Rat-Liver Mitochondria By Synthesized Antimycin A Analog," *Biochimica et Biophysica Acta* 1142:262-268 (1993).
Tzung et al., "Antimycin A Mimics A BH3 Domain-Containing Peptide And Selectively Induces Apoptosis In Cell Lines Overexpressing Bcl-xl3," *Proc. Accr-NCI EORTC International Conference, Molecular Targets And Cancer Therapeutics* 38155-38165 (1999).
Bernardi et al., "The permeability transition pore. Control points of a cyclosporine A-sensitive mitochondrial channel involved in cell death," *Biochim. Biophys. Acta* 1275:5-9 (1996).
Charlotte et al., "Immunohistochemical detection of *bcl-2* protein in normal and pathological human liver," *Am. J. Pathol.* 144:460-65 (1994).
Cheng et al., "Conversion of Bcl-2 to a Bax-like death effector by caspases," *Science* 278:1966-68 (1997).
Chittenden et al., "A conserved domain in Bak, distinct from BH1 and BH2, mediates cell death and protein binding functions," *EMBO J.* 14:5589-96 (1995).
Clem et al., "Modulation of cell death by $Bcl-X_L$ through caspase interaction," *Proc. Natl. Acad. Sci. USA* 95:554-59 (1998).
Cosulich et al., "Regulation of apoptosis by BH3 domains in a cell-free system," *Curr Biol.* 7:913-20 (1997).
Cosulich et al., "Bcl-2 regulates amplification of caspase activation by cytochrome c," *Curr Biol.* 9:147-50 (1999).
Decaudin et al., "Bcl-2 and $Bcl-X_L$ antagonize the mitochondrial dysfunction preceding nuclear apoptosis induced by chemotherapeutic agents," *Cancer Res.* 57:62-67 (1997).
Fisher et al., "Apoptosis in cancer therapy: crossing the threshold," *Cell* 78:539-42 (1994).
Holinger et al., "Bak-BH3 peptides antagonize $Bcl-X_L$ function and induce apoptosis through cytochrome c-independent activation of caspases," *J Biol. Chem.* 274:13298-304 (1999).
Hu et al., "$Bcl-X_L$ interacts with Apaf-1 and inhibits Apaf-1-dependent caspase-9 activation," *Proc. Natl. Acad. Sci. USA* 95:4386-91 (1998).
Hueber et al., "Thy-1 triggers mouse thymocyte apoptosis through a *bcl-2*-resistant mechanism," *J. Exp. Med.* 179:785-96 (1994).
Hunter et al., "A peptide sequence from Bax that converts Bcl-2 into an activator of apoptosis," *J. Biol. Chem.* 271:8521-24 (1996).
Kelekar et al., "Bcl-2-family proteins: the role of the BH3 domain in apoptosis," *Trends Cell Biol*. 8:324-30 (1998).
Kluck et al., "The release of cytochrome c from mitochondria: a primary site for Bcl-2 regulation of apoptosis," *Science* 275:1132-36 (1997).

(Continued)

*Primary Examiner*—Amelia A. Owens
(74) *Attorney, Agent, or Firm*—Townsend and Townsend and Crew LLP

(57) ABSTRACT

The present invention provides agents and compositions for modulating the apoptotic state of a cell. The agents comprise derivatives of antimycins which bind to an anti-apoptotic Bcl-2 family member protein. Further, the agents preferentially induce apoptosis in cells that over-express anti-apoptotic Bcl-2 family member proteins and typically exhibit reduced binding affinity for cytochrome B. Pharmaceutical uses of the agents and compositions include treating apoptosis-associated disease, such as neoplasia and drug resistance, are also disclosed.

8 Claims, 1 Drawing Sheet

OTHER PUBLICATIONS

Kroemer et al., "Mitochondrial control of apoptosis," *Immunol. Today* 18:44-51 (1997).

Kroemer, "The proto-oncogene Bcl-2 and its role in regulating apoptosis," *Nature Med.* 3:614-20 (1997).

Liu et al., "Induction of apoptotic program in cell-free extracts: requirement of dATP and cytochrome c," *Cell* 86:147-57 (1996).

Memon et al., "Bcl-2 blocks glucocorticoid- but not Fas- or activation-induced apoptosis in a T cell hybridoma," *J. Immunol.* 155:4644-52 (1995).

Minn et al., "Expression of Bcl-$x_L$ can confer a multidrug resistance phenotype," *Blood* 86:1903-10 (1995).

Miyoshi et al., "A model of antimycin A binding based on structure-activity studies of synthetic antimycin A analogues," *Biochim. Biophys. Acta* 1229:149-54 (1995).

Muchmore et al., "X-ray and NMR structure of human Bcl-$X_L$ an inhibitor of programmed cell death," *Nature* 381:335-41 (1996).

Newmeyer et al., "Cell-free apoptosis in Xenopus egg extracts: inhibition by Bcl-2 and requirement for an organelle fraction enriched in mitochondria," *Cell* 79:353-64 (1994).

Pan et al., "Caspase-9, Bcl-$X_L$, and Apaf-1 form a ternary complex," *J. Biol. Chem.* 273:5841-5 (1998).

Petit et al., "Mitochondria and programmed cell death: back to the future," *FEBS Letters* 396:7-13 (1996).

Rieske, "Inhibitors of respiration at energy-coupling site 2 of the respiratory chain," *Pharm Ther.* 11:415-50 (1980).

Sattler et al., "Structure of Bcl-$x_L$ -Bak peptide complex: recognition between regulators of apoptosis," *Science* 275:983-86 (1997).

Shimano et al., "Total synthesis of the antifungal dilactones UK-2A and UK-3A: the determination of their relative and absolute configurations, analog synthesis and antifungal activities," *Tetrahedron* 54:12745-74 (1998).

Susin et al., "Bcl-2 inhibits the mitochondrial release of an apoptogenic protease," *J. Exp. Med.* 184:1331-41 (1996).

Susin et al., "The central executioner of apoptosis: multiple connections between protease activation and mitochondria in Fas/APO-1/CD95- and ceramide-induced apoptosis," *J. Exp. Med.* 186:25-37 (1997).

Tokutake et al., "Inhibition of electron transport of rat-liver mitochondria by synthesized antimycin A analogs," *Biochim. Biophys. Acta* 1142:262-68 (1993).

Tokutake et al., "Structural factors of antimycin A molecule required for inhibitor action," *Biochim. Biophys. Acta* 1185:271-79 (1994).

Tzung et al., "Expression of Bcl-2 family during liver regeneration and identification of Bcl-x as delayed early response gene," *Am. J. Pathol.* 150:1985-95 (1997).

van Tamelen et al., "The chemistry of antimycin A. X. Structure of the Antimycins," *J. Am. Chem. Soc.* 83:1639-1646 (1961).

Wu et al., "Establishment and characterization of differentiated, nontransformed hepatocyte cell lines derived from mice transgenic for transforming growth factor α," *Proc. Natl. Sci. USA* 91:674-78 (1994).

Wu et al., "Autonomous growth in serum-free medium and production of hepatocellular carcinomas by differentiated hepatocyte lines that overexpress transforming growth factor α," *Cancer Res.* 54:5964-73 (1994).

Xia et al., "Electrical stimulation of neonatal cardiomyocytes results in the sequential activation of nuclear genes governing mitochondrial proliferation and differentiation," *Proc. Natl. Acad. Sci. USA* 94:11399-404 (1997).

Zamzami et al., "Sequential reduction of mitochondrial transmemberane potential and generation of reactive oxygen species in early programmed cell death," *J. Exp. Med.* 182:367-77 (1995).

Zamzami et al., "Inhibitors of permeability transition interfere with the disruption of the mitochondrial transmembrane potential during apoptosis," *FEBS Letters* 384:53-57 (1996).

Zamzami et al., "Mitochondrial control of nuclear apoptosis," *J. Exp. Med.* 183:1533-44 (1996).

Zoratti et al., "The mitochondrial permeability transition," *Biochim. Biophys. Acta* 1241:139-76 (1995).

* cited by examiner

COMPOSITIONS AND METHODS FOR MODULATING APOPTOSIS IN CELLS OVER-EXPRESSING BCL-2 FAMILY MEMBER PROTEINS

BACKGROUND OF THE INVENTION

Mitochondria play a central role in mediating apoptosis in a number of apoptotic models (Kroemer et al., *Immunol. Today* 18:44–51 (1997); Zamzami et al., *J. Exp. Med.* 183:1533–44 (1996); Zamzami et al., *J. Exp. Med.* 182:367–77 (1995)). Cells induced to undergo apoptosis show an early disruption of mitochondrial transmembrane potential ($\Delta\Psi_m$) preceding other changes of apoptosis, such as nuclear fragmentation and exposure of phosphatidylserine on the outer plasma membrane. Isolated mitochondria or released mitochondrial products induce nuclear apoptosis in a cell-free reconstituted system (Liu et al., *Cell* 86:147–57 (1996); Newmeyer et al., *Cell* 79:353–64 (1994)).

Previous experiments indicated that the pre-apoptotic $\Delta\Psi_m$ loss involves the opening of mitochondrial permeability transition (PT) pores, which are high-conductance channels at the inner mitochondrial membrane corresponding to mitochondrial megachannels identified by electrophysiological studies (Kroemer et al., supra; Zamzami et al. (1996), supra; Bernardi et al., *Biochim. et Biophys. Acta* 1275:5–9 (1996); Zoratti et al., *Biochim. et Biophys. Acta* 1241:139–76 (1995); Petit et al., *FEBS Letters* 396:7–13 (1996)). In fact, induction of PT is sufficient to provoke the full spectrum of apoptosis-associated changes. Conversely, agents that prevent opening of PT pores, such as bongkrekic acid, attenuate apoptosis (Kroemer et al., *Immunol. Today* 18:44–51 (1997); Zamzami et al., *J. Exp. Med.* 183:1533–44 (1996); Zamzami et al., *FEBS Letters* 384:53–57 (1996)).

Members of the evolutionarily conserved Bcl-2 family are important regulators of apoptotic cell death and survival. The proteins Bcl-2, Bcl-$x_L$, Bcl-w, A1 and Mcl-1 are death antagonists while Bax, Bak, Bad, Bcl-xs, Bid, and Bik are death agonists (Kroemer et al., *Nature Med.* 6:614–20 (1997)). Bcl-2 family member proteins are predominantly localized in the outer mitochondrial membrane, but are also found in the nuclear membrane and endoplasmic reticulum (Kroemer et al., supra).

Among Bcl-2 family member proteins, there are several conserved amino acid motifs, BH1–BH4. The pro-apoptotic members of the family, Bax and Bad, contain a BH3 domain that is sufficient to induce cell death (Chittenden et al., *EMBO J.* 14:5589–96 (1995); Hunter et al., *J. Biol. Chem.* 271:8521–24 (1996)). Interestingly, the BH3 domain is conserved in the anti-apoptotic proteins Bcl-2 and Bcl-$x_L$. Recently, it was reported that cleavage of Bcl-$x_L$ and Bcl-2 in the loop domain removes the N-terminal BH4 domain and converts Bcl-$x_L$ and Bcl-2 into a potent pro-death molecule (Cheng et al., *Science* 278:1966–68 (1997); Clem et al., *Proc. Nat. Acad. Sci. USA* 95:554–59 (1998)).

NMR structure analysis of a complex between Bcl-$x_L$ and a 16 residue peptide encompassing the Bak BH3 domain demonstrated that the BH3 peptide, in an amphipathic alpha-helical configuration, binds with high affinity to the hydrophobic pocket created by the BH1, BH2 and BH3 domains of Bcl-$x_L$ (Sattler et al., *Science* 275:983–86 (1997)). Leucine at position 1 of the BH3 domain core and aspartic acid at position 6 are believed to be critical residues for both heterodimerization and apoptosis induction. In further support of this conclusion, a number of "BH3 only" death promoters have been identified which have no similarity to Bcl-2 beyond their BH3 domain homology (Kelekar et al., *Trends Cell Biol.* 8:324–30 (1998)). These include Bik, Bim, Hrk, Bad, Blk, and Bid, which cannot homodimerize, but rely on binding to anti-apoptotic proteins such as Bcl-2 to induce cell death.

The exact mechanisms by which Bcl-2 prevents apoptosis remain elusive. In light of the importance of mitochondria in apoptosis and the mitochondrial location of Bcl-2, it appears that one major site where Bcl-2 interrupts apoptotic signals is at the level of mitochondria. It has been shown that Bcl-2 inhibits apoptosis by preventing mitochondrial permeability transition and by stabilizing $\Delta\Psi$m (Zamzami et al., *J. Exp. Med.* 183:1533–44 (1996)). In the absence of Bcl-2, apoptogenic factors, such as cytochrome c and apoptosis inducing factor (AIF), are released from mitochondria in response to apoptotic triggers (Susin et al., *J. Exp. Med.* 184:1331–41 (1996); Kluck et al., *Science* 275:1132–36 (1997)). This release in turn leads to sequential caspase activation and results in nuclear and membrane changes associated with apoptosis.

Bcl-2 family members display a distinct tissue-specific expression. In adult human liver, Bcl-2 expression is confined to bile duct cells (Charlotte et al., *Am. J. Pathol.* 144:460–65 (1994)) and is absent in both normal and malignant hepatocytes. In contrast, expression of Bcl-$x_L$ RNA and protein can be detected in adult quiescent hepatocytes and increases by 4 to 5 fold during the G1 phase of regenerating hepatocytes (Tzung et al., *Am. J. Pathol.* 150:1985–95 (1997)). Increased Bcl-$x_L$ expression is also observed in hepatoma cell lines, such as HepG2.

Some diseases are believed to be related to the down-regulation of apoptosis in the affected cells. For example, neoplasias may result, at least in part, from an apoptosis-resistant state in which cell proliferation signals inappropriately exceed cell death signals. Furthermore, some DNA viruses, such as Epstein-Barr virus, African swine fever virus and adenovirus, parasitize the host cellular machinery to drive their own replication and at the same time modulate apoptosis to repress cell death and allow the target cell to reproduce the virus. Moreover, certain diseases, such as lymphoproliferative conditions, cancer (including drug resistant cancer), arthritis, inflammation, autoimmune diseases, and the like, may result from a down regulation of cell death signals. In such diseases, it would be desirable to promote apoptotic mechanisms.

Most cancer chemotherapeutic agents that are currently available target cellular DNA and induce apoptosis in tumor cells (Fisher et al., *Cell* 78:539–42 (1994)). A decreased sensitivity to apoptosis induction has emerged as an important mode of drug resistance. In particular, over-expression of Bcl-2 and Bcl-$x_L$ confers resistance to multiple chemotherapeutic agents, including alkylating agents, antimetabolites, topoisomerase inhibitors, microtubule inhibitors and anti-tumor antibiotics, and may constitute a mechanism of clinical chemoresistance in certain tumors (Minn et al., *Blood* 86:1903–10 (1995); Decaudin et al., *Cancer Res.* 57:62–67 (1997)).

Neither Bcl-2 nor Bcl-$x_L$, however, protects cells from every apoptotic inducer. For example, over-expression of Bcl-2 offers little protection against Thy-1-induced thymocyte death and Fas-induced apoptosis (Hueber et al., *J. Exp. Med.* 179:785–96 (1994); Memon et al., *J. Immunol.* 15:4644–52 (1995)). At the mitochondrial level, Bcl-2 over-expressed in the outer mitochondrial membrane inhibits PT pore induction by t-butyl-hydroperoxide, protonophore and atractyloside, but not by calcium ions, diamide or caspase 1 (Zamzami et al., *J. Exp. Med.* 183:1533–44 (1996); Susin et al., *J. Exp. Med.* 186:25–37 (1997)). Thus, one class of mitochondrially-active agents may directly affect the mitochondrial apoptosis machinery while bypassing the site of Bcl-2 function and the protection offered by Bcl-2 family members. An agent of this type may potentially be useful in overcoming the multi-drug resistance imparted by Bcl-2 or Bcl-$x_L$ and are of great need in the art.

The antimycins constitute another class of mitochondrially-active agents. The antimycins generally comprise a N-formylamino salicylate moiety linked to a dilactone ring through an amide bond. The antimycins differ in the hydrophobic R groups attached to the dilactone ring opposite the amide bond. (See, e.g., Rieske, *Pharm. Ther.* 11:415–20 (1980).) For example, antimycin $A_1$ has a hexyl group at the 2 position of the dilactone ring while antimycin $A_3$ has a butyl group at that position.) Extensive literature has been published on the structure-activity relationship of the antimycins and their inhibition of cytochrome $bc_1$ (Miyoshi et al., *Biochim. Biophys. Acta* 1229:149–54 (1995); Tokutake et al., *Biochim. Biophys. Acta* 1142:262–68 (1993); Tokutake et al., *Biochim. Biophys. Acta* 1185:271–78 (1994)). The published structure of cytochrome $bc_1$ complex with bound antimycin $A_1$ reveals that antimycin $A_1$ occupies a position in the Qi ubiquinone binding site on cytochrome b (Xia et al., *Proc. Nat. Acad. Sci. USA* 94:11399–404 (1997)). The antimycins generally inhibit mitochondrial respiration, which suggests that the differences in the hydrophobic R groups on the dilactone ring are not critical for cytochrome b binding. Mutagenesis and structure-activity studies of antimycin A demonstrate that the cytochrome $bc_1$-inhibitory activity is highly dependent on the N-formylamino salicylic acid moiety (Tokutake et al. (1994), supra). Methylation of the phenolic hydroxyl or modification of the N-formylamino group both significantly reduce the ability of antimycin A to bind to and inhibit cytochrome $bc_1$. Methylation of the phenolic hydroxyl diminishes inhibitory activity by 2.5 logs. Substitution of the formylamino group with acetylamino and propylamino groups at the 3-position reduce cytochrome $bc_1$ activity by 1.2 and 2.4 logs, respectively. Thus, the N-formylamino salicylate moiety is generally understood to be important for binding of the antimycins to cytochrome b.

Two antimycins, antimycin $A_1$ and $A_3$, have recently been discovered to inhibit the activity of the anti-apoptotic Bcl-2 family member proteins, Bcl-2 or Bcl-$x_L$. Thus, these molecules potentially useful compounds for the medical profession and patients suffering from proliferative disease and other diseases where apoptosis is inappropriately regulated. The antimycins are toxic, however, because they also inhibit mitochondrial respiration. There is a critical need, therefore, for derivatives of the antimycins that are effective in inducing apoptosis in cells where apoptosis is inappropriately regulated while exhibiting reduced inhibition of mitochondrial respiration.

SUMMARY OF THE INVENTION

The present invention is based on the surprising discovery that the antimycins can inhibit the activity of anti-apoptotic Bcl-2 family member proteins, such as Bcl-2 or Bcl-$x_L$. The invention is further based on the discovery that mitochondrial respiratory inhibitory activity, of the antimycins, is separable from the inhibition of the Bcl-2 family member proteins.

The present invention provides agents comprising derivatives of antimycins that modulate apoptosis by binding to a Bcl-2 family member protein. These agents exhibit reduced binding to cytochrome B (or the cytochrome $bc_1$ complex, hereafter referred to as "cytochrome B") as compared with non-derivatized antimycins. In one embodiment, the agent preferentially induces apoptosis in cells that over-express an anti-apoptotic Bcl-2 family member protein. In another embodiment, the agent is substantially non-toxic to cells that do not over-express the anti-apoptotic Bcl-2 family member protein. The agent typically inhibits the activity of an anti-apoptotic Bcl-2 family member protein by binding to the hydrophobic pocket formed by the BH1, BH2 and BH3 domains of the protein.

The agents comprises derivatives of an antimycin, or a portion thereof, such as chemical modification of the N-formylamino salicylic acid moiety (e.g., salicylic acid or acetylsalicylic acid), and/or the dilactone moiety (i.e., the 4,9-dioxo-1,5-dioxanan-7-yl ester moiety). In a preferred embodiment, the antimycin derivative comprises at least two chemical modifications. One modification decreases the affinity of the antimycin derivative for cytochrome B. The second modification increases the affinity of the antimycin derivative for a Bcl-2 family member protein.

In another aspect, the invention provides methods for modulating apoptosis in a cell. Such methods generally comprise administering an agent to modulate apoptosis in the cell. In one embodiment, the agent preferentially induces apoptosis in a cell that over-expresses an anti-apoptotic Bcl-2 family member protein. The agent typically exhibits reduced binding affinity for cytochrome B. In a preferred embodiment, the agent is substantially non-toxic to cells that do not over-express the anti-apoptotic Bcl-2 family member protein. The agent comprises a derivative of an antimycin, or a portion of an antimycin, such as derivatives of the N-formylamino salicylic acid moiety (e.g., salicylic acid or acetylsalicylic acid,) or the dilactone moiety. In another embodiment, the method comprises administering the agent to inhibit the activity of the anti-apoptotic Bcl-2 family member protein by binding to the hydrophobic pocket formed by the BH1, BH2 and BH3 domains of the protein.

In another aspect, the invention provides pharmaceutical compositions comprising the agent, as well as the use of such pharmaceutical compositions, for treating a subject in which a cell over-expresses an anti-apoptotic Bcl-2 family member protein. Such compositions and methods are useful for treating apoptosis-associated diseases or conditions, such as drug-resistance. In a preferred embodiment, the compositions and use thereof preferentially induce apoptosis in cells that over-express the anti-apoptotic Bcl-2 family member protein. The agent typically exhibits reduced binding affinity for cytochrome B. In a preferred embodiment, the agent is substantially non-toxic to cells that do not over-express the anti-apoptotic Bcl-2 family member protein.

The present invention further provides methods for assaying candidate compounds to identify agents that modulate the activity of a Bcl-2 family member protein. The methods generally comprise the steps of administering the candidate compound to a cell that over-expresses the Bcl-2 family member protein; administering the candidate compound to another cell that does not over-express the Bcl-2 family member protein; and determining whether the candidate compound modulates the activity of the Bcl-2 family member protein to produce a physiological change in the cell that over-expresses the Bcl-2 family member protein, but does not produce a substantial physiological change in the cell which does not over-express that protein. In a preferred embodiment, the Bcl-2 family member protein is anti-apoptotic. Cells that over-express the anti-apoptotic Bcl-2 family member protein, such as Bcl-$x_L$ or Bcl-2, are produced by, for example, transfection with a gene or cDNA fragment that encodes the protein. The cells can be any mammalian cell and in a particular embodiment are murine liver cells. Physiological changes that are indicative of binding of the candidate compound to the Bcl-2 family member protein (e.g., in the hydrophobic pocket) include an affect on cell death, cell shrinkage, chromosome condensation and migration, mitochondria swelling, and/or disruption of mitochondrial transmembrane potential.

DESCRIPTION OF THE SPECIFIC EMBODIMENTS

Figure 1:
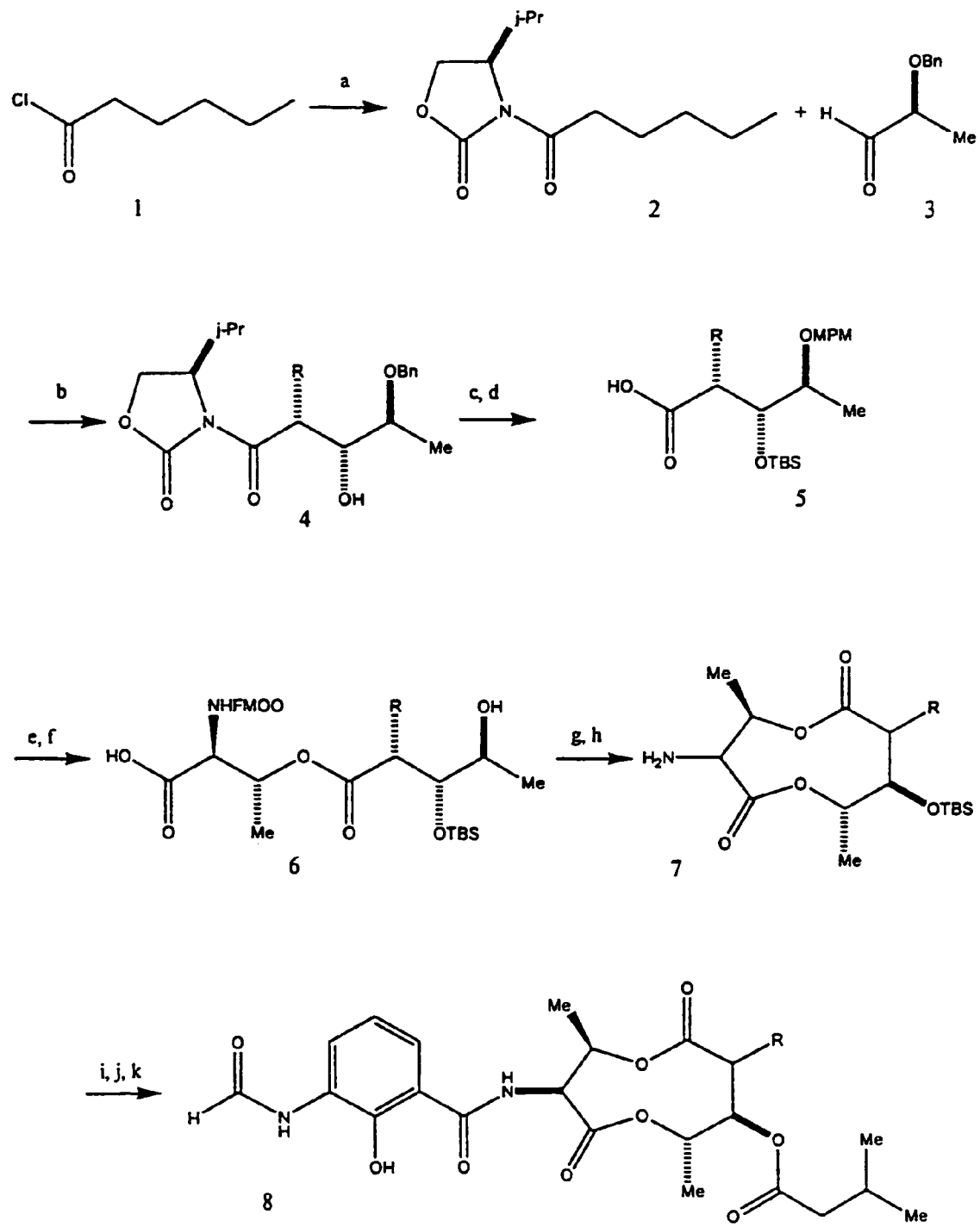
FIG. 1 depicts a general scheme for the chemical synthesis of antimycin $A_3$, and for the synthesis of derivatives of antimycins.

Prior to setting forth the invention in more detail, it may be helpful to a further understanding thereof to set forth definitions of certain terms as used hereinafter.

Definitions:

The term "apoptosis" refers to a regulated network of biochemical events which lead to a selective form of cell suicide, and is characterized by readily observable morphological and biochemical phenomena, such as the fragmentation of the deoxyribo-nucleic acid (DNA), condensation of the chromatin, which may or may not be associated with endonuclease activity, chromosome migration, margination in cell nuclei, the formation of apoptotic bodies, mitochondrial swelling, widening of the mitochondrial cristae, opening of the mitochondrial permeability transition pores and/or dissipation of the mitochondrial proton gradient.

The term "antimycins" refers to the antimycins $A_{0\,(a-d)}$, $A_1$, $A_2$, $A_3$, $A_4$, $A_5$, $A_6$, kitamycin A and B, urauchimycin B, deisovaleryl blastomycin, and dehexyl-deisovaleryloxy antimycin A. The antimycins are generally represented by the following formula I, and have the absolute configuration [2R, 3R, 4S, 7S, 8R]:

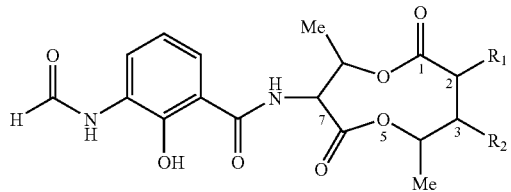

(I)

The groups at positions R1 and R2 vary as follows:

TABLE 1

| Name | $R_1$ | $R_2$ |
|---|---|---|
| antimycin $A_{0(a)}$ | hexyl | hexanoic acid |
| antimycin $A_{0(b)}$ | butyl | heptanoic acid |
| antimycin $A_{0(c)}$ | octyl | butanoic acid |
| antimycin $A_{0(d)}$ | heptyl | isovaleric acid |
| antimycin $A_{1b}$ | hexyl | isovaleric acid |
| antimycin $A_2$ | hexyl | butanoic acid |
| antimycin $A_3$ | butyl | isovaleric acid |
| antimycin $A_4$ | butyl | butanoic acid |
| antimycin $A_5$ | ethyl | isobutanoic acid |
| antimycin $A_6$ | ethyl | butanoic acid |
| kitamycin A | hexyl | hydroxyl |

TABLE 1-continued

| Name | $R_1$ | $R_2$ |
|---|---|---|
| kitamycin B | isohexyl | hydroxyl |
| urauchimycin B | isohexyl | hydroxyl |
| deisovalerylblastomycin | butyl | hydroxyl |
| dehexyl-deisovalerylblastomycin | hydrogen | hydrogen |

The term "antimycin derivative" refers to a chemical modification of an antimycin, by which one or more atoms of an antimycin are removed or substituted, or new atoms are added. An "antimycin derivative" further includes portions of an antimycin as well as chemical modifications thereof, and chiral variants of an antimycin.

The term "agent" is used herein to denote a chemical compound, or a mixture of chemical compounds, salts and solvates thereof, and the like, which are capable of modulating the biological activity of a Bcl-2 family member protein. An agent typically comprises an antimycin derivative.

The term "preferentially induce" apoptosis refers to at least a 5-fold greater stimulation of apoptosis, at a given concentration of an agent, in cells that over-express a Bcl-2 family member protein as compared with cells that do not over-express the Bcl-2 family member protein (e.g., a 5-fold greater $LD_{50}$ or $IC_{50}$).

The term "substantially non-toxic" refers to an agent that induces apoptosis in at least about 50 percent of cells that over-express a Bcl-2 family member protein, but does not induce apoptosis in more than about 5%, more preferably less than 1%, of cells that do not over-express the Bcl-2 family member protein.

The term "Bcl-2 family member protein(s)" refers to an evolutionarily conserved family of proteins characterized by having one or more amino acid homology domains, BH1, BH2, BH3, and/or BH4. The Bcl-2 family member proteins include Bcl-2, Bcl-$x_L$, Bcl-w, A1, Mcl-1, Bax, Bak, Bad, Bcl-xs and Bid. The "Bcl-2 family member proteins" further include those proteins, or their biologically active fragments, that are at least 70% similar in amino acid sequence to a Bcl-2 family member protein.

The term "anti-apoptotic Bcl-2 family member protein" refers to Bcl-2, Bcl-$x_L$, Bcl-w, A1, Mcl-1, and other proteins characterized by having one or more amino acid homology domains, BH1, BH2, BH3, and/or BH4, and that promote cell survival by attenuating or inhibiting apoptosis. The "anti-apoptotic Bcl-2 family member proteins" further include those proteins, or their biologically active fragments, that are at least 70% similar in amino acid sequence to an anti-apoptotic Bcl-2 family member protein.

The terms "identical" or "percent identity," in the context of two or more nucleic acids or polypeptide sequences, refer to two or more sequences or subsequences that are the same or have a specified percentage of nucleotides or amino acids that are the same, when compared and aligned for maximum correspondence, as measured using one of the following sequence comparison algorithms, or by visual inspection.

The term "substantially identical," in the context of two nucleic acids, or two polypeptide sequences, refers to two or more sequences or subsequences that have at least 60%, typically 80%, most typically 90–95% identity, when compared and aligned for maximum correspondence, as measured using one of the sequence comparison algorithms described below, or by visual inspection. An indication that two polypeptide sequences are "substantially identical" is that one polypeptide is immunologically reactive with antibodies raised against the second polypeptide.

"Similarity" or "percent similarity" in the context of two or more polypeptide sequences, refer to two or more sequences or subsequences that are the same or have a specified percentage of amino acid residues, or conservative substitutions thereof, that are the same when compared and aligned for maximum correspondence, as measured using one of the following sequence comparison algorithms, or by visual inspection. By way of example, a first protein region can be considered similar to a region of an anti-apoptotic Bcl-2 family member protein when the amino acid sequence of the first region is at least 70%, 75%, 80%, 90%, or even 95% identical, or conservatively substituted, to a region of the second anti-apoptotic Bcl-2 family member protein when compared to any sequence of an equal number of amino acids as the number contained in the first region, or when compared to an alignment of anti-apoptotic Bcl-2 family member proteins that has been aligned by a computer similarity program known in the art, as discussed below.

The term "substantial similarity" in the context of polypeptide sequences, indicates that the polypeptide comprises a sequence with at least 70% sequence identity to a reference sequence, or preferably 80%, or more preferably 85% sequence identity to the reference sequence, or most preferably 90% identity over a comparison window of about 10–20 amino acid residues. In the context of amino acid sequences, "substantial similarity" further includes conservative substitutions of amino acids. Thus, a polypeptide is substantially similar to a second polypeptide, for example, where the two peptides differ only by one or more conservative substitutions.

The terms "amino acid," "amino acid residue," or "residue" refer to naturally occurring L amino acids or to D amino acids. Amino acids are referred to herein by either their commonly known three letter symbols or by the one-letter symbols recommended by the IUPAC-IUB Biochemical Nomenclature Commission. Nucleotides, likewise, may be referred to by their commonly accepted single-letter codes. (See e.g., Alberts et al., *Molecular Biology of the Cell*, Garland Publishing, Inc., New York (3d ed. 1994), incorporated herein by reference).

The term "conservative substitution," when describing a polypeptide, refers to a change in the amino acid composition of the polypeptide that does not substantially alter the polypeptide's activity. Thus, a "conservative substitution" of a particular amino acid sequence refers to a substitution of one or more amino acids that are not critical for biological activity or substitution of one or more amino acids with other amino acids having similar properties (e.g., acidic, basic, positively or negatively charged, polar or non-polar, and the like) such that the substitution of even critical amino acids does not substantially alter activity. Conservative substitution tables providing functionally similar amino acids are well known in the art. The following six groups each contain amino acids that are conservative substitutions for one another: 1) Alanine (A), Serine (S), Threonine (T); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); and 6) Phenylalanine (F), Tyrosine (Y), Tryptophan (W). (See also Creighton, Proteins, W.H. Freeman and Company (1984), incorporated herein by reference.) In addition, individual substitutions, deletions or additions that alter, add or delete a single amino acid or a small percentage of amino acids in an encoded sequence are also considered "conservative substitutions."

For sequence comparison, typically one sequence acts as a reference sequence, to which test sequences are compared. When using a sequence comparison algorithm, test and reference sequences are typically input into a computer, coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, for example, by the local homology algorithm of Smith & Waterman (*Adv. Appl. Math.* 2:482 (1981), incorporated herein by reference), by the homology alignment algorithm of Needleman & Wunsch (*J. Mol. Biol.* 48:443 (1970), incorporated herein by reference), by the search for similarity method of Pearson & Lipman (*Proc. Nat. Acad. Sci. USA* 85:2444 (1988), incorporated herein by reference), by computerized implementations of these algorithms (e.g., GAP, BESTFIT, FASTA, and TFASTA in the Wisconsin Genetics Software Package, Genetics Computer Group, 575 Science Dr., Madison, Wis., incorporated herein by reference), or by visual inspection. (See generally Ausubel et al., *Current Protocols in Molecular Biology*, John Wiley and Sons, New York (1996), incorporated herein by reference).

One example of a useful algorithm is PILEUP. PILEUP creates a multiple sequence alignment from a group of related sequences using progressive, pairwise alignments to show the percent sequence identity. It also plots a tree or dendogram showing the clustering relationships used to create the alignment. PILEUP uses a simplification of the progressive alignment method of Feng & Doolittle (*J. Mol. Evol.* 35:351–60 (1987), incorporated herein by reference). The method used is similar to the method described by Higgins & Sharp (*CABIOS* 5:151–53 (1989), incorporated herein by reference). The program can align up to 300 sequences, each of a maximum length of 5,000 nucleotides or amino acids. The multiple alignment procedure begins with the pairwise alignment of the two most similar sequences, producing a cluster of two aligned sequences. This cluster is then aligned to the next most related sequence or cluster of aligned sequences. Two clusters of sequences are aligned by a simple extension of the pairwise alignment of two individual sequences. The final alignment is achieved by a series of progressive, pairwise alignments. The program is run by designating specific sequences and their amino acid or nucleotide coordinates for regions of sequence comparison and by designating the program parameters. For example, a reference sequence can be compared to other test sequences to determine the percent sequence identity relationship using the following parameters: default gap weight (3.00), default gap length weight (0.10), and weighted end gaps.

Another example of an algorithm that is suitable for determining percent sequence identity and similarity is the BLAST algorithm, which is described by Altschul et al. (*J. Mol. Biol.* 215:403–10 (1990), incorporated herein by reference). (See also Zhang et al., *Nucleic Acid Res.* 26:3986–90 (1998); Altschul et al., *Nucleic Acid Res.* 25:3389–402 (1997), both of which are incorporated herein by reference.) Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990), supra). These initial neighborhood word hits act as seeds for initiating searches to find longer HSPs containing them. The word hits are then extended in both directions along each sequence for as far as the cumulative alignment score can be increased. Extension of the word hits in each direction is halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLAST program uses as defaults a wordlength (W) of 11, the BLOSUM62 scoring matrix (see Henikoff& Henikoff, *Proc. Nat. Acad. Sci. USA* 89:10915–19 (1992), incorporated herein by reference), alignments (B) of 50, expectation (E) of 10, M=5, N=−4, and a comparison of both strands.

In addition to calculating percent sequence identity, the BLAST algorithm also performs a statistical analysis of the similarity between two sequences (see, e.g., Karlin & Altschul, *Proc. Nat. Acad. Sci. USA* 90:5873–87 (1993), incorporated herein by reference). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more typically less than about 0.01, and most typically less than about 0.001.

A further indication that two nucleic acid sequences or polypeptides are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions.

The terms "biologically active" or "biological activity" refer to the ability of a molecule to modulate apoptosis, such as by binding to a Bcl-2 family member protein. A biologically active molecule can modulate apoptosis by causing a change in the mitochondrial proton gradient (see e.g., Example 2), by causing a change in mitochondrial swelling or the morphological characteristics of mitochondria (see, e.g., Example 2), by affecting the release of a reporter molecule, such as, for example, rhodamine 123 or calcein, from mitochondria or vesicles (see, e.g., Examples 4 and 8) comprising a pore-forming anti-apoptotic Bcl-2 family member protein (see, e.g., Example 8), or by causing any other morphological change associated with apoptosis.

The terms "therapeutically useful" and "therapeutically effective" refer to an amount of an agent that effectively modulates the apoptotic state of an individual cell, such that the inappropriately regulated cell death cycle in the cell returns to a normal state, and/or that apoptosis is induced.

The terms "diagnostically useful" and "diagnostically effective" refer to an agent (e.g., an antimycin derivative) for detecting the induction or inhibition of apoptosis in a subject. These terms further include molecules useful for detecting diseases associated with apoptosis, or the susceptibility to such diseases, and for detecting over-expression or under-expression of a Bcl-2 family member protein.

The terms "over-expression" and "under-expression" refer to increased or decreased levels of a Bcl-2 family member protein, respectively, in a cell, as compared with the level of such a protein found in the cell under normal physiological conditions.

The term "apoptosis-associated disease" includes diseases, disorders and conditions that are linked to an increased or decreased state of apoptosis in at least some of the cells of a subject. Such diseases include neoplastic disease (e.g., cancer and other proliferative diseases), tumor formation, arthritis, inflammation, autoimmune disease, human immunodeficiency virus (HIV) immunodeficiency syndrome, neurodegenerative diseases, myelodysplastic syndromes (such as aplastic anemia), ischaemic syndromes (such as myocardial infarction), liver diseases which are induced by toxins (such as alcohol), alopecia, damage to the skin due to UV light, lichen planus, atrophy of the skin, cataract and graft rejections. Neurodegenerative diseases include Alzheimer's disease, Parkinson's disease, amyotrophic lateral sclerosis and other diseases linked to degeneration of the brain, such as Creutzfeldt-Jakob disease. Apoptosis-associated diseases further include drug resistance associated with increased or decreased levels of a Bcl-2 family member protein, and also includes multiple chemotherapeutic drug resistance.

Agents:

The present invention provides agents that modulate apoptosis of a cell by binding to a Bcl-2 family member protein. In one embodiment, the present invention is directed to agents comprising derivatives of an antimycin that modulate apoptosis by binding to a Bcl-2 family member protein. The agents typically exhibit reduced binding affinity to cytochrome B, as compared with the non-derivatized antimycin. Typically such agents preferentially induce apoptosis in cells that over-express the Bcl-2 family member protein. Such agents preferably are substantially non-toxic to cells that do not over-express the anti-apoptotic Bcl-2 family member protein.

In one embodiment, the derivatives of antimycin are those with a chemical modification of the antimycin, such as a chemical modification of the salicylate moiety and/or the dilactone moiety. Such derivatives can be prepared by chemically modifying an antimycin. Examples of suitable chemical modifications include addition, removal or substitution of the following substituents:

(1) hydrocarbon substituents, such as aliphatic (e.g., linear or branched alkyl, alkenyl, or alkynyl), alicyclic (e.g., cycloalkyl, or cycloalkenyl) substituents, aromatic, aliphatic and alicyclic-substituted aromatic nuclei, and the like, as well as cyclic substituents;

(2) substituted hydrocarbon substituents, such as those substituents containing nonhydrocarbon radicals which do not alter the predominantly hydrocarbon substituent; those skilled in the art will be aware of such radicals (e.g., halo (especially bromo, chloro, fluoro, or iodo), alkoxy, acetyl, carbonyl, mercapto, alkylmercapto, sulfoxy, nitro, nitroso, amino, alkyl amino, amide, and the like);

(3) hetero substituents, that is, substituents which will, while having predominantly hydrocarbyl character, contain other than carbon atoms. Suitable heteroatoms will be apparent to those of ordinary skill in the art and include, for example, sulfur, oxygen, hydroxyl, nitrogen, and such substituents as, for example, pyridyl, furanyl, thiophenyl, imidazolyl, and the like. Heteroatoms, and typically no more than one, will be present for each carbon atom in the hydrocarbon-based substituents. Alternatively, there can be no such radicals or heteroatoms in the hydrocarbon-based substituent and it will, therefore, by purely hydrocarbon.

In one embodiment, the antimycin derivative is of the following formula II:

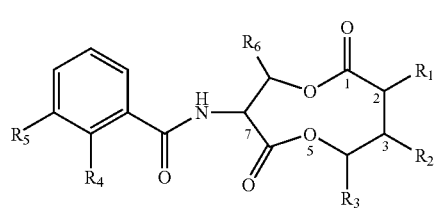

where each of positions $R_1$–$R_6$ can be independently modified. For example, each of $R_{1-R6}$ can independently be hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), amino, an amino halogen salt (e.g., amino chloride, amino bromide or amino fluoride), a $C_1$–$C_8$ di- or tri-alkylamine (e.g., methyl amine, dimethyl amine, ethyl amine, diethyl amine, and the like), a $C_1$–$C_8$ amide (e.g., formylamino, acetylamino, propylamino, and the like), a $C_1$–$C_8$ carboxylic acid (e.g., formic acid, acetic acid, propionic acid, butryic acid, isobutyric acid, pentanoic acid, isopentanoic acids (e.g., isovaleric acid), hexanoic acid, isohexanoic acids, heptanoic acid, isoheptanoic acids, octanoic acid, isooctanoic acids, and the like), and a substituted alkyl group (e.g., an alkyl group containing an additional substituent, such as cyano, nitro, chloro, bromo, iodo, and the like).

In another embodiment, the antimycin derivative comprises at least one of the following chemical modifications. According to formula II, $R_1$ to $R_6$ are typically as follows:

$R_1$ is hydrogen, $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like);

$R_2$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like);

$R_3$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like);

$R_4$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), or a substituted alkyl group (e.g., an alkyl group containing an additional substituent, such as cyano, nitro, chloro, bromo, iodo, and the like);

$R_5$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), amino, a $C_1$–$C_8$ di- or tri-amine (e.g., methyl amine, dimethyl amine, ethyl amine, diethyl amine, and the like), a $C_1$–$C_8$ amide (e.g., N-formylamino, N-acetylamino, and the like), a $C_1$–$C_8$ carboxylic acid (e.g., formic, acetic acid, propionic acid, butanoic acid, isobutanoic acid, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like); and $R_6$ is hydrogen, $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (, an alkyl group containing an additional substituent, such as cyano, nitro, chloro, bromo, iodo, and the like);

with the proviso that the antimycin derivative is not antimycin $A_{0\ (a\text{-}d)}$, $A_1$, $A_2$, $A_3$, $A_4$, $A_5$, $A_6$ kitamycin A or B, urauchimycin B, deisovaleryl blastomycin, dehexyl-deisovaleryloxy antimycin A, 2-methoxy ether antimycin $A_3$, deformyl antimycin $A_1$ or $A_3$, antimycin diacetate $A_3$, deformyl antimycin triacetate $A_3$, deformyl-N-acetyl antimycin $A_3$, or deformyl-N-bromo-acetyl antimycin $A_3$. (See Rieske, supra, which is incorporated by reference herein in its entirety.)

In another embodiment, the antimycin derivative comprises at least two chemical modifications. One chemical modification reduces the affinity of the derivative for cytochrome B. The second chemical modification is in $R_1$–$R_3$ or $R_6$ (i.e. in the dilactone moiety).

Suitable chemical modifications, according to formula II, that decrease the affinity of the derivative for cytochrome B include, but are not limited to, one or more of the following:

$R_4$ is hydrogen, a $C_1$–$C_8$ linear or branched alkane (e.g., methyl, ethyl, butyl, isobutyl, pentyl, isopentyl, and the like), a $C_1$–$C_8$ hydroxyalkane (e.g., hydroxymethyl, hydroxyethyl, hydroxypropyl, and the like), or a substituted alkyl group (e.g., an alkyl group containing an additional substituent, such as cyano, nitro, chloro, bromo, iodo, and the like); and $R_5$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), amino, a $C_3$–$C_8$ di- or tri-alkylamine (e.g., ethyl amine, diethyl amine, and the like), a $C_1$–$C_8$ carboxylic acid (e.g., formic, acetic acid, propionic acid, butanoic acid, isobutanoic acid, pentanoic acid, isopentanoic acids (e.g., isovaleric acid), hexanoic acid, isohexanoic acids, heptanoic acid, isoheptanoic acids, octanoic acid, isooctanoic acids, and the like), a $C_2$–$C_8$ amide (e.g., N-acetylamino, N-propylamino, N-butyrylamino, N-isobutyrylamino, N-pentanylamino, N-isopentanylamino, and the like); or a substituted alkyl group (e.g., an alkyl group containing an additional substituent, such as cyano, nitro, chloro, bromo, iodo, and the like).

Suitable chemical modifications of the dilactone moiety include, but are not limited to, one or more of the following:

$R_1$ is hydrogen, $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like);

$R_2$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g., isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like);

$R_3$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), a $C_1$–$C_8$ amide (e.g., N-formylamino, N-acetylamino, and the like), a $C_1$–$C_8$ carboxylic acid (e.g., formic acid, acetic acid, propionic acid, butanoic acid, isobutanoic acids, pentanoic acid, isopentanoic acids (e.g. isovaleric acid), hexanoic acid, isohexanoic acids, heptanoic acid, isoheptanoic acids, octanoic acid, isooctanoic acids, and the like), or a substituted alkyl group (e.g., an alkyl group containing an additional substituent, such as cyano, nitro, chloro, bromo, iodo, and the like); and $R_6$ is hydrogen, a $C_1$–$C_8$ linear or branched alkane (e.g., methyl, ethyl, butyl, isobutyl, pentyl, isopentyl, and the like), hydroxyl, a $C_1$–$C_8$ hydroxyalkane (e.g., hydroxymethyl, hydroxyethyl, hydroxypropyl, and the like), amino, a $C_1$–$C_8$ di- or tri-amine (e.g., methyl amine, dimethyl amine, ethyl amine, diethyl amine, and the like), or a substituted alkyl group (e.g., an alkyl group containing an additional substituent, such as cyano, nitro, chloro, bromo, iodo, and the like);

with the proviso that the antimycin derivative is not 2-methoxy ether antimycin $A_3$, deformyl antimycin $A_1$ or $A_3$, antimycin diacetate $A_3$, deformyl antimycin triacetate $A_3$, a deformyl-N-acetyl antimycin $A_3$, or deformyl-N-bromo-acetyl antimycin $A_3$. (See Rieske, supra, which is incorporated by reference herein in its entirety.)

Antimycin derivatives can be prepared by chemically modifying an antimycin according to standard chemical methods. For example, the hydroxyl group on the salicylate moiety of antimycin $A_3$ can be modified using a primary alkyl halide or diazomethane to form a 2-alkoxy ether antimycin derivative (e.g., 2-methoxy ether antimycin $A_3$). An antimycin can also be modified by acetylation.

Alternatively, antimycin derivatives can be prepared by de novo ("total") chemical synthesis. For example, Shimano et al. (*Tetrahedron* 54:12745–74 (1998), which is incorporated by reference herein in its entirety) have devised a total synthetic method for the related antifungal dilactones UK-2A and UK-3A. This total synthesis can be used to prepare antimycin derivatives. According to this method, antimycin $A_3$ can be modeled as comprising three structural units: N-formyl-3-aminosalicylic acid, L-threonine, and the dilactone moiety. (See formulae III–V, respectively.)

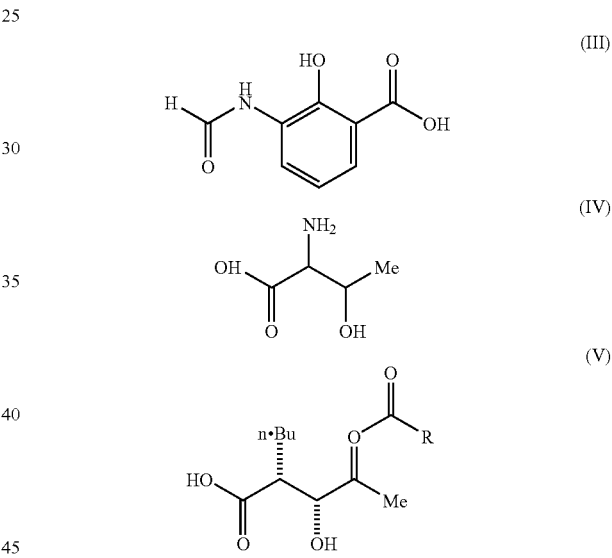

Antimycin $A_3$ can be synthesized by joining these structural units. Derivatives of one or more of these structural units can be chemically linked to form antimycin derivatives. For example, suitable derivatives of N-formyl-3-aminosalicylic acid include, but are not limited to, salicylic acid, 2-hydroxyl-3-amino-benzoic acid, N-acetyl-3-aminosalicylic acid, N-propionyl-3-aminosalicylic acid, and N-butyryl-3-aminosalicylic acid, as well as various 2-hydroxyl-3-alkyl-benzoic acids. Derivatives of L-threonine include L-serine, 2-amino-3-hydroxy-propionic acid, 2-amino-3-hydroxy-hexanoic acid, and the like. Derivatives of the dihydroxypentanoic acid can be prepared by chemical synthesis, as more fully described in the Examples.

In another embodiment, the agent is a portion of an antimycin, such as one of the functional moieties of an antimycin. Such an antimycin derivative can be a derivative of the N-formyl amino salicylic acid moiety, the threonine moiety or the dilactone moiety.

For example, the agent can be a chemical modification of N-formyl-3-amino salicylic acid (Formula III), such as salicylic acid, 2-hydroxyl-3-amino-benzoic acid, N-acetyl-3-aminosalicylic acid, N-propionyl-3-aminosalicylic acid, N-butyryl-3-aminosalicylic acid, as well as various 2-hydroxyl-3-alkyl-benzoic acids. Derivatives of the threonine moiety (formula IV) include serine, 2-amino-3-hydroxy-propionic acid, 2-amino-3-hydroxy-hexanoic acid, and the like. Similarly, derivatives of the dilactone moiety can be prepared as further described in the Examples.

Libraries of antimycin derivatives can also be prepared by rational design. (See generally Cho et al., *Pac. Symp. Biocompat.* 305–16 (1998); Sun et al., *J. Comput. Aided Mol. Des.* 12:597–604 (1998); each incorporated herein by reference in their entirety). For example, libraries of antimycin derivatives can be prepared by syntheses of combinatorial chemical libraries (see generally DeWitt et al., *Proc. Nat. Acad. Sci. USA* 90:6909–13 (1993); International Patent Publication WO 94/08051; Baum, *Chem. & Eng. News,* 72:20–25 (1994); Burbaum et al., *Proc. Nat. Acad. Sci. USA* 92:6027–31 (1995); Baldwin et al., *J. Am. Chem. Soc.* 117:5588–89 (1995); Nestler et al., *J. Org. Chem.* 59:4723–24 (1994); Borehardt et al., *J. Am. Chem. Soc.* 116:373–74 (1994); Ohlmeyer et al., *Proc. Nat. Acad. Sci. USA* 90:10922–26 (1993); and Longman, *Windhover's In Vivo The Business & Medicine Report* 12:23–31 (1994), all of which are incorporated by reference herein in their entirety.)

The following articles describe methods for selecting starting molecules and/or criteria used in their selection: Martin et al., *J. Med. Chem.* 38:1431–36 (1995); Domine et al., *J. Med. Chem.*, 37:973–80 (1994); Abraham et al., *J. Pharm. Sci.* 83:1085–100 (1994); each of which is hereby incorporated by reference in its entirety.

A "combinatorial library" is a collection of compounds in which the compounds comprising the collection are composed of one or more types of subunits. The subunits can be selected from natural or unnatural moieties, including dienes, benzene compounds, cycloalkanes, lactones, dilactones, amino acids, alkanes, and the like. The compounds of the combinatorial library differ in one or more ways with respect to the number, order, type or types of modifications made to one or more of the subunits comprising the compounds. Alternatively, a combinatorial library may refer to a collection of "core molecules" which vary as to the number, type or position of R groups they contain and/or the identity of molecules composing the core molecule. The collection of compounds is generated in a systematic way. Any method of systematically generating a collection of compounds differing from each other in one or more of the ways set forth above is a combinatorial library.

A combinatorial library can be synthesized on a solid support from one or more solid phase-bound resin starting materials. The library can contain five (5) or more, preferably ten (10) or more, organic molecules which are different from each other (i.e., five (5) different molecules and not five (5) copies of the same molecule). Each of the different molecules (different basic structure and/or different substituents) will be present in an amount such that its presence can be determined by some means (e.g., can be isolated, analyzed, detected with a binding partner or suitable probe). The actual amounts of each different molecule needed so that its presence can be determined can vary due to the actual procedures used and can change as the technologies for isolation, detection and analysis advance. When the molecules are present in substantially equal molar amounts, an amount of 100 picomoles or more can be detected. Preferred libraries comprise substantially equal molar amounts of each desired reaction product and do not include relatively large or small amounts of any given molecules so that the presence of such molecules dominates or is completely suppressed in any assay.

Combinatorial libraries are generally prepared by derivatizing a starting compound onto a solid-phase support (such as a bead). In general, the solid support has a commercially available resin attached, such as a Rink or Merrifield Resin. After attachment of the starting compound, substituents are attached to the starting compound. For example, a benzene compound can be bound to a support via a Rink resin. The benzene ring is reacted simultaneously with an amide, such as a N-formylamino, N-acetylamino, N-propionylamino, and the like. Alternatively, the starting compound can comprise the dilactone moiety, or a precursor thereof. Substituents are added to the starting compound, and can be varied by providing a mixture of reactants comprising the substituents. Examples of suitable substituents include, but are not limited to, the following:

(1) hydrocarbon substituents, that is, aliphatic (e.g., alkyl or alkenyl), alicyclic (e.g. cycloalkyl, cycloalkenyl) substituents, aromatic, aliphatic and alicyclic-substituted aromatic nuclei, and the like, as well as cyclic substituents;

(2) substituted hydrocarbon substituents, that is, those substituents containing nonhydrocarbon radicals which do not alter the predominantly hydrocarbon substituent; those skilled in the art will be aware of such radicals (e.g., halo (especially chloro and fluoro), alkoxy, mercapto, alkylmercapto, nitro, nitroso, sulfoxy, and the like);

(3) hetero substituents, that is, substituents which will, while having predominantly hydrocarbyl character, contain other than carbon atoms. Suitable heteroatoms will be apparent to those of ordinary skill in the art and include, for example, sulfur, oxygen, nitrogen, and such substituents as pyridyl, furanyl, thiophenyl, imidazolyl, and the like. Heteroatoms, and typically no more than one, will be present for each carbon atom in the hydrocarbon-based substituents. Alternatively, there may be no such radicals or heteroatoms in the hydrocarbon-based substituent and it will, therefore, by purely hydrocarbon.

In one embodiment, a combinatorial library of derivatives of antimycins is prepared. For example, the starting compound can be a precursor of the dilactone moiety. A combinatorial library of the dilactone is synthesized using the Shimano synthesis (infra) while varying the substituents added at each step of the synthesis. Optionally, following lactonization, the threonine and salicylic acid moieties, or derivatives thereof, are added to the library.

Methods of making combinatorial libraries are known in the art, and include the following: U.S. Pat. Nos. 5,958,792; 5,807,683; 6,004,617; 6,077,954; which are incorporated by reference herein.

Methods of Identifying Agents

Methods are also provided to identify agents that modulate apoptosis. In one embodiment, the method generally comprises the steps of administering a candidate compound to a cell that over-expresses the Bcl-2 family member protein; administering the candidate compound to another cell that does not over-express the Bcl-2 family member protein; and determining whether the candidate compound modulates the activity of the Bcl-2 family member protein to produce a physiological change in the cell that over-expresses the Bcl-2 family member protein, but does not produce a substantial physiological change in the cell which does not over-express that protein. Physiological changes that are indicative of binding of the candidate compound to the Bcl-2 family member protein (e.g., in the hydrophobic pocket) include an affect on cell death, cell shrinkage, chromosome condensation and migration, mitochondria swelling, and/or disruption of mitochondrial transmembrane potential (i.e., the mitochondrial proton gradient), and/or cell death (e.g., trypan dye exclusion).

In one example, a candidate compound is added to mammalian tissue culture cells over-expressing a Bcl-2 family member protein, to cells having normal levels of the Bcl-2 family member protein, and to control cells to which no compound is added. Methods of expressing Bcl-2 family member proteins in tissue culture cells are well known in the art. (See e.g., Example 1, U.S. Pat. No. 5,998,583.) At various time points after administration of the candidate compound (e.g., at 6 and 24 hours), the cells from each group are trypsinized, and cell viability is determined by trypan blue dye exclusion. The number of viable cells are counted and normalized to control group (i.e., % control=no. of viable cells (treated group)/no. of viable cells (control group)×100). The candidate compound that is effective as an anti-apoptotic agent preferentially induces apoptosis in cells over-expressing the Bcl-2 family member protein, but not cells having normal levels of the Bcl-2 family member protein.

In another example, the candidate compound is added to mammalian tissue culture cells over-expressing a Bcl-2 family member protein, to cells having normal levels of the Bcl-2 family member protein and to control cells, to which no compound is added. At various time points after administration of the candidate compound (e.g., at 6 and 24 hours), nuclear morphology is determined by DAPI staining. Cells in which apoptosis has occurred will exhibit characteristic changes in nuclear morphology, such as chromosome condensation and migration. Methods to monitor other physiological changes are disclosed in the Examples (infra).

In another embodiment, reagents and assay conditions which are useful for interrogating agents for utility in the present invention comprise: (1) cells which over-express an anti-apoptotic Bcl-2 family member (e.g., Bcl-2, Bcl-$x_L$, Bcl-w, A1, Mcl-1, and the like), (2) aqueous components which produce binding conditions, e.g., physiological buffers, (3) a reporter system, e.g., a cell, or a reporter molecule, and (4) a candidate compound being tested. The candidate compound can also be screened for toxicity to cells that do not over-express the anti-apoptotic Bcl-2 family member protein.

Candidate compounds are initially screened for modulation of activity of cells that over-express the Bcl-2 family member protein. In one particular embodiment, a candidate compound is identified by its ability to preferentially induce apoptosis in cells transformed with a gene which encodes at least the Bcl-$x_L$ BH3 binding domain. The candidate compound is then further tested for the absence of, or reduced induction of, apoptosis in a control cell, which does not over-express the anti-apoptotic Bcl-2 family member protein (e.g., one that has not been so transformed, or that is transformed with a control vector, or an anti-sense vector). A successful candidate compound is one which induces apoptosis preferentially in a cell which over-expresses Bcl-$x_L$. In particular embodiment, candidate compounds are assayed for their ability to preferentially induce apoptosis in a murine tumorigenic liver cell line which over-expresses the Bcl-$x_L$ protein.

In another embodiment, the ability of a candidate compound to modulate pore forming activity by a Bcl-2 family member protein is determined. This assay comprises a membrane enclosed vesicle, the vesicle having on its surface a Bcl-2 family member protein, such as Bcl-$x_L$ or the Bcl-2. A reporter present within the vesicle acts as an indicator of the modulation of pore formation by the candidate compound. Suitable reporters include fluorescers, chemiluminescers, radiolabels, enzymes, enzyme cofactors, and the like.

One specific example of this assay comprises preparing large unilamellar vesicles (LUV's) containing a fluorescent reporter molecule. In a particular embodiment, LUV's (e.g., comprising 60% dioleophosphatidylcholine and 40% dioleoylphosphatidyl-glycerol) contain the fluorescent reporter calcein. When an anti-apoptotic Bcl-2 family member protein is inserted into the vesicle, the fluorescent reporter leaks out of the vesicle. Binding of a candidate compound being tested to the anti-apoptotic Bcl-2 family member protein disrupts pore formation, and leakage of the reporter from the vesicle is blocked.

In yet another assay system, agents are identified by their ability to bind to the BH3 binding domain of a Bcl-2 family member protein, such as Bcl-2 or Bcl-$x_L$ polypeptide, under binding conditions. In particular, the fluorescence changes associated with antimycin-binding to the BH3-binding domain of an anti-apoptotic Bcl-2 family member is exploited to identify BH3-binding domain ligands. As discussed in more detail in the Examples, the antimycins have a natural fluorescence (e.g., antimycin $A_1$ and $A_3$ fluoresce at 428 nm). The fluorescence of the antimycin increases when it binds to the hydrophobic pocket of a Bcl-2 family member protein. The fluorescence intensity of the antimycin bound to the hydrophobic pocket of Bcl-2 is titratable with BH3 peptide. A candidate compound that displaces the antimycin from the hydrophobic pocket of Bcl-$x_L$ is indicated by the decrease in the amount of fluorescence (e.g., at 428 nm). Thus, a candidate compound found to displace the BH3 peptide, or an antimycin in a manner equivalent to that of BH3 peptide, in this assay is a candidate for additional testing for modulation of pore formation and/or cell toxicity.

In another assay system, the ability of a candidate compound to compete with BH3-peptide for binding to the BH3-binding domain of an anti-apoptotic Bcl-2 family member protein is exploited to identify BH3-binding domain ligands. In one example, the ability of a candidate compound to compete with the BH3 peptide for binding to the hydrophobic pocket is measured by displacement of labeled BH3 peptide. Suitable labels include fluorescers, chemiluminescers, radiolabels, enzymes, enzyme cofactors, and the like. After addition of the candidate compound under suitable binding conditions, the amount labeled BH3 peptide remaining bound to the Bcl-2 family member protein is determined. Such an assay is useful both for identifying compounds that inhibit the biological activity of the Bcl-2 family member protein and to identify compounds that block binding of pro-apoptotic Bcl-2 family member proteins to the anti-apoptotic protein without affecting the biological activity.

In other embodiments, combinatorial libraries of candidate compounds e.g., antimycin derivatives) can be screened for biological activity using any of the methods described herein. For example, combinatorial library compounds that modulate apoptosis, or that bind to Bcl-2 family member proteins, can be identified. One such method for testing a candidate compound for the ability to bind to and potentially modulate apoptosis is as follows: exposing at least one candidate compound from the combinatorial library to a Bcl-2 family member protein for a time sufficient to allow binding of the combinatorial library compound to the protein; removing non-bound compound; and determining the presence of the candidate compound bound to the protein.

Another method utilizing this approach that may be pursued in the identification of such candidate compounds includes the attachment of a combinatorial library, or a portion thereof, to a solid matrix, such as agarose or plastic beads, microtiter wells, petri dishes, or membranes composed of, for example, nylon or nitrocellulose, and the subsequent incubation of the attached combinatorial library molecule in the presence of a Bcl-2 family member protein. Attachment to the solid support can be direct or by means of a combinatorial-library-compound-specific antibody bound directly to the solid support. After incubation, unbound compounds are washed away, and protein-bound compounds are recovered. By utilizing this procedure, large numbers of candidate compounds can be simultaneously screened for Bcl-2 family member protein-binding activity.

In a preferred embodiment, the agent (e.g., an antimycin derivative) exhibits reduced binding affinity for cytochrome B. Candidate compounds can be screened for such reduced binding affinity for cytochrome B. Methods for measuring binding to cytochrome B include measuring the effect of the candidate compound on cytochrome $bc_1$ activity according to the methodology described by Miyoshi et al. (*Biochim. Biophys. Acta* 1229:149–54 (1995), the disclosure of which is incorporated by reference herein). Briefly, submitochondrial particles are prepared from bovine heart mitochondria according to standard methods. (See, e.g., Matsuno-Yagi and Hatefi, *J. Biol. Chem.* 260:14424–27 (1985), the disclosure of which is incorporated by reference herein.) The particles are treated with sodium deoxycholate (0.3 mg/mg protein) before dilution with reaction buffer. (See, e.g., Esposti and Lenaz, *Biochim. Biophys. Acta* 682:189–200 (1982), the disclosure of which is incorporated by reference herein.) Cytochrome $bc_1$ complex activity is measured at 30° C. as the rate of cytochrome c reduction with DBH as an electron donor. The reaction buffer can comprise 0.25 M sucrose, 1 mM $MgCl_2$, 2 mM KCN, 20 μM cytochrome c and 50 mM phosphate buffer (pH 7.4). The final mitochondrial protein concentration is 15 μg/ml.

In another embodiment, ATP production by mitochondria is measured as a measure of cytochrome B activity. Briefly, the candidate compound is added to the cells. After a 1 hour incubation, cells are harvested, and intracellular ATP concentrations are determined, for example, by an ATP-dependent luciferase-luciferin assay (Sigma, St. Louis, Mo.). An antimycin, such as A, and/or $A_3$, is used as a control. Reduced cytochrome B binding is indicated by a smaller reduction in intracellular ATP levels by the candidate compound than by the antimycin control.

Methods of Using the Agents

Agents of the present invention are useful for treating cells in which the cell death signal is down regulated and the affected cell has an inappropriately diminished propensity for cell death, which is referred to herein as being in a "decreased apoptotic state." The invention further provides methods for the administration to a subject of a therapeutically effective amount of an agent to treat an apoptosis-associated disease in which it is desirable to induce apoptosis in certain types of cells, such as virus-infected or autoantibody-expressing cells. Typically, the agent is substantially purified prior to administration. The subject can be an animal, including but not limited to, cows, pigs, horses, chickens, cats, dogs, and the like, and is typically a mammal, and in a particular embodiment human. In another specific embodiment, a non-human mammal is the subject.

In one embodiment, the agent comprises an antimycin of formula I, such as those identified in Table 1 (supra), and/or those of formula II (supra). In another one embodiment, the antimycin derivative is of formula II and exhibits reduced binding for cytochrome B (see supra). In another embodiment, the antimycin derivative exhibits reduced binding affinity for cytochrome B and comprises additional modifications of the dilactone moiety (see supra).

Various delivery systems are known and can be used to administer an agent, such as, for example, encapsulation in liposomes, microparticles, microcapsules, recombinant cells capable of expressing the agent, receptor-mediated endocytosis (see, e.g., Wu and Wu, *J. Biol. Chem.* 262:4429–32 (1987)), and the like. The agents administered as therapeutic or pharmaceutical compositions by any suitable route known to the skilled artisan including, for example, intravenous, subcutaneous, intramuscular, intradermal, transdermal, intrathecal, intracerebral, intraperitoneal, epidural and oral routes. Administration can be either rapid as by injection or over a period of time as by slow infusion or administration of slow release formulations. For treating tissues in the central nervous system, administration can be by injection or infusion into the cerebrospinal fluid (CSF). When it is intended that an agent be administered to cells in the central nervous system, administration can be with one or more other components capable of promoting penetration of the agent across the blood-brain barrier. In addition, it can be desirable to introduce an agent into the target tissue by any suitable route, including intravenous and intrathecal injection. Pulmonary administration can also be employed, such as, for example, by use of an inhaler or nebulizer, and formulation of the agent with an aerosolizing agent.

Pharmaceutical compositions can also be administered orally in any orally acceptable dosage form including, but not limited to, capsules, tablets, caplets, lozenges, aqueous suspensions or solutions. In the case of tablets for oral use, carriers which are commonly used include lactose and corn starch. Lubricating aids, such as magnesium stearate, are also typically added. For oral administration in a capsule form, useful diluents include lactose and dried corn starch. When aqueous suspensions are required, the agent can be combined with emulsifying and suspending aids. If desired, certain sweeteners, flavorants or colorants can also be used.

In a specific embodiment, it can be desirable to administer the agent locally to the area in need of treatment; this administration can be achieved by, for example, and not by way of limitation, local infusion during surgery, topical application (e.g., in conjunction with a wound dressing after surgery), by injection, by means of a catheter, by means of a suppository, or by means of an implant, the implant being of a porous, non-porous, or gelatinous material, including membranes such as silastic membranes, or fibers. In one embodiment, administration can be by direct injection at the site (or former site) of a malignant tumor or neoplastic or pre-neoplastic tissue.

In another embodiment, the agent can be delivered in a vesicle, in particular a liposome (see, e.g., Langer, Science 249:1527–33 (1990); Treat et al., *In Liposomes in the Therapy of Infectious Disease and Cancer*, Lopez-Berestein and Fidler (eds.), Liss, New York, pp. 353–65 (1989); Lopez-Berestein, supra, pp. 317–27).

In yet another embodiment, the agent can be delivered in a controlled release system. In one embodiment, a pump can be used (see, e.g., Langer, supra; Sefton, *CRC Crit. Ref. Biomed. Eng.* 14:201 (1987); Buchwald et al., *Surgery* 88:507 (1980); Saudek et al., *N. Engl. J. Med.* 321:574 (1989)). In another embodiment, polymeric materials can be used (see, e.g., *Medical Applications of Controlled Release*, Langer and Wise (eds.), CRC Pres., Boca Raton, Fla. (1974);

*Controlled Drug Bioavailability, Drug Product Design and Performance*, Smolen and Ball (eds.), Wiley, New York (1984); Ranger and Peppas, *J. Macromol. Sci. Rev. Macromol. Chem.* 23:61 (1983); see also Levy et al., *Science* 228:190 (1985); During et al., *Ann. Neurol.* 25:351 (1989); Howard et al., *J. Neurosurg.* 71:105 (1989)). In yet another embodiment, a controlled release system can be placed in proximity of the therapeutic target, thus requiring only a fraction of the systemic dose (see, e.g., Goodson, *Medical Applications of Controlled Release*, supra, Vol. 2, pp. 115–138 (1984)). Other controlled release systems are discussed in, for example, the review by Langer (*Science* 249:1527–33 (1990)).

The present invention also provides pharmaceutical compositions. Such compositions comprise a therapeutically effective amount of an agent, and a pharmaceutically acceptable carrier. The term "pharmaceutically acceptable" means approved by a regulatory agency of the Federal or a state government or listed in the U.S. Pharmacopeia or other generally recognized pharmacopeia for use in animals, and more typically in humans. The term "carrier" refers to a diluent, adjuvant, excipient, stabilizer, or vehicle with which the agent is formulated for administration. Pharmaceutical carriers can be sterile liquids, such as water and oils, including those of petroleum, animal, vegetable or synthetic origin, such as peanut oil, soybean oil, mineral oil, sesame oil, and the like. Water is a typical carrier when the pharmaceutical composition is administered intravenously. Saline solutions and aqueous dextrose and glycerol solutions can also be employed as liquid carriers, particularly for injectable solutions. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The composition, if desired, can also contain minor amounts of wetting or emulsifying agents, or pH buffering agents. Pharmaceutical compositions can take the form of solutions, suspensions, emulsion, tablets, pills, capsules, powders, sustained-release formulations, and the like. The composition can be formulated as a suppository, with traditional binders and carriers such as triglycerides.

Oral formulations can include standard carriers such as pharmaceutical grades of mannitol, lactose, starch, magnesium stearate, sodium saccharine, cellulose, magnesium carbonate, and the like. Examples of suitable pharmaceutical carriers are described in, for example, *Remington's Pharmaceutical Sciences*, by E. W. Martin. Such compositions will contain a therapeutically effective amount of the agent, typically in purified form, together with a suitable amount of carrier so as to provide a formulation proper for administration to the subject. The formulation should suit the mode of administration.

In one embodiment, the agent is formulated in accordance with routine procedures as a pharmaceutical composition adapted for intravenous administration to human beings. Typically, compositions for intravenous administration are solutions in sterile isotonic aqueous buffer. Where necessary, the composition can also include a solubilizing agent and a local anesthetic to ease pain at the site of the injection. Generally, the ingredients are supplied either separately or mixed together in unit dosage form. For example, as a dry lyophilized powder or water-free concentrate in a hermetically sealed container such as an ampoule or sachette indicating the quantity of active agent. Where the composition is to be administered by infusion, it can be dispensed with an infusion bottle containing sterile pharmaceutical grade water or saline. Where the composition is administered by injection, an ampoule of sterile water for injection or saline can be provided so that the ingredients can be mixed prior to administration.

The agents of the invention can be formulated as neutral or salt forms. Pharmaceutically acceptable salts include those formed with free amino groups such as those derived from hydrochloric, phosphoric, acetic, oxalic, tartaric acids, and the like, and those formed with free carboxyl groups such as those derived from sodium, potassium, ammonium, calcium, ferric hydroxides, isopropylamine, triethylamine, 2-ethylamino ethanol, histidine, procaine, and the like.

The amount of the agent that is combined with the carrier to produce a single dosage form will vary, depending upon the nature of that agent and the composition of the dosage form. It should be understood, however, that a specific dosage and treatment regime for any particular patient, or disease state will depend upon a variety of factors, including the age, body weight, general health, sex, diet, time of administration, rate of excretion, drug combination, the judgment of the treating physician, and the severity of the particular disease being treated. The amount of active agent will also depend upon the specific activity of the agent and whether the agent is co-administered with any other therapeutic or prophylactic ingredients. Dosage levels of between about 0.001 and about 100 mg/kg body weight per day, typically between about 0.1 and about 10 mg/kg body weight per day of the active agent are useful.

The invention also provides a pharmaceutical pack or kit comprising one or more containers filled with one or more of the ingredients of the pharmaceutical compositions of the invention. Optionally associated with such container(s) can be a notice in the form prescribed by a governmental agency regulating the manufacture, use or sale of pharmaceuticals or biological products, which notice reflects approval by the agency of manufacture, use or sale for human administration.

The following examples are provided merely as illustrative of various aspects of the invention and shall not be construed to limit the invention in any way.

EXAMPLE 1

To examine the sensitivity of cells over-expressing Bcl-$x_L$ to various mitochondrial inhibitors and apoptosis inducers, cell lines over-expressing Bcl-$x_L$ were prepared and tested.

Briefly, a DNA fragment encoding the full-length mouse Bcl-$x_L$ cDNA was isolated from the plasmid pBS.BCL-$x_L$ (Tzung et al., *Am. J. Path.* 150:1985–95 (1997), incorporated herein by reference in its entirety) by digestion with the restriction endonuclease EcoRI. This EcoRI fragment was cloned into the EcoRI site of the mammalian expression vector pSFFV (Fuhlbrigge et al., *Proc. Nat. Acad. Sci. USA* 85:5649–53 (1988)) in both sense and antisense orientations, to form expression plasmids pSFFV.Bcl-$x_L$(sense) or pSFFV.Bcl-$x_L$(antisense), respectively. The tumorigenic murine hepatocyte cell line TAMH was transfected by lipofection (Lipofectamine, Life Technologies, Rockville, Md., according to the manufacturer's recommendations) with the plasmids pSFFV.neo (the control), pSFFV.Bcl-$x_L$ (sense) or pSFFV.Bcl-$x_L$(antisense). Characterization of and culture conditions for the cell lines have been previously published (Wu et al., *Proc. Nat. Acad. Sci. USA* 91:674–78 (1994); Wu et al., *Cancer Res.* 54:5964–73 (1994), each incorporated herein by reference in its entirety). Transfectants were selected for the acquisition of neomycin resistance by growing cells in the presence of 750 μg/ml of G418.

Bulk transfectants were cloned by limiting dilution and individual clones were screened by immunoblot analysis to determine the level of Bcl-$x_L$ protein expression as described below.

Bcl-$x_L$ protein expression was determined by Western blot analysis. Cell pellets or purified mitochondrial pellets were lysed in 1% Triton X-100, 5 mM Tris (pH 8.0) and 150 mM NaCl. Each lane was loaded with 20 µg of protein and electrophoresed (120 V) on a 12% SDS-polyacrylamide gel. Proteins were then electrically transferred to a nitrocellulose membrane. Immunodetection was performed using the rabbit anti-Bcl-$x_L$ polyclonal antibody 13.6 (Gottschalk et al. *Proc. Nat. Acad. Sci. USA* 91:7350 (1994), which is incorporated by reference herein in its entirety) followed by a biotinylated goat anti-rabbit antibody (Vector, Burlingame, Calif.; 1:500 dilution) and horseradish peroxidase conjugated streptavidin (Zymed, S. San Francisco, Calif.; 1:1000 dilution). Chemiluminescence (ECL, Amersham, Arlington Heights, Ill.) was used for detection. Expression of Bcl-$x_L$ expression was indicated by the appearance of a band of approximately 29 kDa.

Bcl-$x_L$ protein levels were determined by comparing the intensity of the 29 kDa band on a Western (immunoblot) blot between selected transfectants and the parental TAMH hepatocyte cell line. TABX2S cells (transfected with PSFFV.Bcl-$x_L$ (sense)) was found to express a 4- to 5-fold higher level of Bcl-$x_L$ protein as compared with the parental (control) TAMH.neo cells. The antisense transfectant TABX1A (transfected with PSFFV.Bcl-$x_L$ (anti-sense)), on the other hand, was found to express little or no Bcl-$x_L$ protein.

Mitochondrial expression of Bcl-$x_L$ protein was examined by Western blot analysis of mitochondrial lysates prepared from TABX2S cells and TABX1A cells. Briefly, mitochondrial pellets were prepared by centrifugation and the pellets were lysed in 1% Triton, 5 mM Tris (pH 8.0) and 150 mM NaCl. Each lane of a 12% SDS-polyacrylamide gel was loaded with 20 µg of protein and electrophoresed (120 V) through the gel. Proteins were then electrically transferred to a nitrocellulose membrane. Detection of Bcl-$x_L$ protein was as described above. Consistent with the results for overall cellular expression of Bcl-$x_L$ protein, the level of mitochondrial Bcl-$x_L$ protein was approximately 6 fold higher in TABX2S (pSFFV.Bcl-$x_L$ (sense)) cells than TAMH.neo cells (control).

Selected transfectants were then tested for whole cell sensitivity to several apoptotic agents. Transfected cells were cultured to reach approximately 80% confluency prior to plating an equal number of cells from selected clones on 12-well tissue culture plates. The transplanted cells were treated with the following apoptotic agents: 5 µM doxorubicin for 48 hours; 5 µM cisplatin for 48 hours; or with 200 U/ml tumor necrosis factor (TNF) plus 1 µg/ml actinomycin D for 18 hours. Cell viability was determined by trypan blue dye exclusion. The percentage of viable cells was calculated by the number of viable cells (treated with a particular apoptogenic agent) divided by the number in the control group (untreated).

The sensitivity of the tested transfectants to treatment with apoptotic agents was inversely correlated with the level of Bcl-$x_L$ expression. Cells over-expressing Bcl-$x_L$ were less sensitive to the apoptogenic agent than control cells. For example, after treatment with doxorubicin (5 µM) for 48 hours, 50% of control TAMH.neo cells (control), 88% of TABX2S cells (over-expressing Bcl-$x_L$) and 20% of TABX1A cells (under-expressing Bcl-$x_L$) remained viable. A similar trend was observed with cisplatin or TNF treatment. Thus, cells over-expressing Bcl-$x_L$ were less sensitive to the apoptogenic agent than control cells, and conversely, cells expressing an anti-sense construct, (pSFFV.Bcl-$x_L$ (antisense)) were more sensitive than control cells.

TABX2S cells and TABX1A cells were also examined for the effects of various mitochondrial inhibitors. To test the apoptotic responses of these cells following direct perturbation of mitochondrial function, the cells were treated with rotenone (a mitochondrial complex I inhibitor), sodium azide (a mitochondrial complex IV inhibitor), antimycin A (a mitochondrial complex III inhibitor), valinomycin (an ionophore), and oligomycin (an ATP synthase or mitochondrial complex V inhibitor). Briefly, antimycin A (Sigma, St. Louis, Mo.) and rotenone were dissolved in DMSO to form a stock solution, while valinomycin and oligomycin were dissolved in chloroform and ethanol, respectively, to form stock solutions. Azide was diluted from an aqueous stock solution. Antimycin A (a mixture of antimycins $A_1$–$A_4$) (0 to 5 µg/ml), rotenone (0 to 2.5 µg/ml), valinomycin (0 to 10 µg/ml), oligomycin (0 to 10 µM), and azide (0 to 2 µM) were serially diluted into culture medium. Controls received an equivalent concentration of diluent. At various time points after drug treatment, cells were trypsinized, and cell viability was determined by trypan blue dye exclusion. The number of viable cells were counted and normalized to control group (i.e., % control=no. of viable cells (treated group)/no. of viable cells (control group)×100).

TABX2S cells were found to be markedly more sensitive than TABX1A and TAMH.neo cells to antimycin A over a wide range of concentrations. When the $LD_{50}$ of antimycin A was estimated from the dose-response curve, a seven-fold difference was found between TABX2S cells ($LD_{50}$=1.2 µM) and TABX1A or TAMH.neo cells ($LD_{50}$=8.3 µM). Following the addition of antimycin A to the cell culture, cell death was readily apparent within 2 hours in TABX2S cells, but not in TABX1A cells. The morphology of the dying cells was examined by light microscopy, which indicated that the TABX2S cells treated with antimycin A had an appearance consistent with apoptosis. The cells were also stained with Annexin V-EGFP and propium iodide, according to the manufacturer's instructions (Clontech, Palo Alto, Calif.). TABX2S cells treated with antimycin A exhibited a redistribution of phosphatidylcholine to the outer plasma membrane, which is consistent with the induction of apoptosis. There were no significant differences in the sensitivity of the two cell lines to rotenone, sodium azide, valinomycin or oligomycin. Furthermore, the cell death induced by rotenone or valinomycin was not apparent until six to eight hours after treatment. Thus, cells over-expressing Bcl-$x_L$ were more sensitive to antimycin A, but not to other mitochondrial inhibitors.

The effects of Bcl-$x_L$ over-expression on non-tumorigenic cells was also examined. In particular, the sensitivity of cells that over-express Bcl-$x_L$ to antimycin A was further examined in the non-tumorigenic mouse liver cell lines, AML-12 (ATCC CRL-2254) and NMH. Briefly, AML-12 cells were transfected as described above with pSFFV.Bcl-$x_L$(sense) and pSFFV.neo. AML-12-pSFFV. Bcl-$x_L$(sense) cells expressed approximately 3 to 4 fold higher Bcl-$x_L$ protein levels than did AML-12 cells tansfected with the control plasmid, pSFFV.neo, when assayed by Western blot analysis. The AML-12.Bcl-$x_L$ cells demonstrated increased sensitivity to antimycin A, which is consistent with the results from TAMH cells. Similar results were also found with the mouse liver cell line NMH and with two other TAMH clones stably transfected with a vector that over-expresses Bcl-$x_L$.

TAMH cells that over-express the related family member protein Bcl-2 were also more sensitive to antimycin A than were control cells.

Thus, cells over-expressing Bcl-$x_L$ or Bcl-2 exhibited increased sensitivity to antimycin A. In particular, this inhibitor preferentially induced apoptosis in Bcl-$x_L$-over-expressing liver cell lines, confirming that certain mitochondrially active agents can overcome or bypass the anti-apoptotic effect of Bcl-$x_L$ over-expression. Since over-expression of Bcl-$x_L$ or Bcl-2 resulted in a decreased apoptotic sensitivity and has been implicated in multidrug resistance in cancer cells and carcinogenesis, this finding has clinical implications. In particular, this difference represents a significant therapeutic window which can be exploited for preferentially inducing apoptosis in cells over-expressing Bcl-$x_L$ or Bcl-2, while cells not over-expressing Bcl-$x_L$ or Bcl-2 are minimally affected.

EXAMPLE 2

In this example various cellular characteristics associated with cell inhibition by antimycin A were examined and correlated with cell death. Specifically, reactive oxygen species ("ROS") and ATP production were examined following antimycin A treatment. Other parameters of mitochondrial function were also measured.

Electrons as reducing equivalents are fed into the mitochondrial electron transport chain at the level of Coenzyme Q (CoQ) from the primary $NAD^+$- and FAD-linked dehydrogenase reaction and are transported sequentially through the cytochrome chain to molecular oxygen. As discussed above, antimycin A inhibits complex III ($CoQH_2$-cytochrome c reductase) downstream of CoQ. Complex III serves as an electron transfer station for transfer of electrons from CoQ to cytochrome c. Because CoQ is the major source of ROS derived from the mitochondrial respiratory chain (Turrens et al., *Arch. Biochem. Biophys.* 237:408–14 (1985)), inhibition of complex III often leads to increased ROS formation. The production of ROS in this example was measured by incubating control or antimycin A-treated cells with dihydroethidium. ROS present in the sample oxidizes dihydroethidium to the fluorescent product, ethidium (Rothe et al., *J. Leukocyte Biol.*, 47:440–48 (1990)).

Briefly, TABX2S and TABX1A cells were harvested and resuspended at $5 \times 10^5$ cells/ml. These cells were incubated with 5 µM dihydroethidium in tissue culture media for 45 minutes at 37° C. and then submitted for flow cytometric analysis. One hour after antimycin A treatment, when apoptosis was not apparent, the levels of ethidium were increased to a similar extent in both TABX2S and TABX1A cells. Similarly, when peroxide levels were measured by incubating the cells with dichlorodihydrofluorescein (H2-DCF-DA), the increase in peroxide production was the same between the two cell lines. Thus, antimycin A treatment did not appear to alter the formation of ROS.

Correlation of ATP production with cell death was examined by comparing the ATP production in antimycin A-treated cells and control cells treated with DMSO vehicle alone. Similarly treated cells were tested for viability by trypan blue dye exclusion. Generally, mitochondrial ATP production is driven by the electrochemical gradient generated along the respiratory chain. Following complex III inhibition by antimycin A, electron flow is blocked and ATP synthesis is interrupted.

To determine whether there is a correlation between ATP production and cell death, TABX2S and TABX1A cells were treated with (1) DMSO, (2) 2 µg/ml antimycin A, or (3) 2 µg/ml antimycin A plus fructose (50 mM added 15 minutes before and 15 minutes after administration of antimycin A). Fructose is a substrate that provides ATP production through the glycolysis pathway. After a 1 hour incubation, cells were harvested and intracellular ATP concentrations were determined by an ATP-dependent luciferase-luciferin assay (Sigma, St. Louis, Mo.). The ATP concentrations in DMSO-treated cells were taken as 100%. In parallel experiments, cell viability was determined after six hours.

Intracellular ATP levels were found to decrease by 70 to 75% in both TABX2S and TABX1A cells within 30 minutes of antimycin A treatment. Supplementation with fructose, a substrate for ATP production through the glycolysis pathway, restored the ATP level to approximately 60% of control, but had no effect on subsequent cell death. Thus, ATP levels did not correlate with the extent of apoptosis. For instance, even though there was a higher ATP level in antimycin A-treated TABX2S cells supplemented with fructose than in antimycin A-treated TABX1A cells without fructose, significantly more apoptosis occurred in the former (33% survival vs. 87% survival). These data argue against a primary role of ATP depletion in mediating apoptosis in antimycin A-treated TAMH cells.

To further test if the mitochondrial respiratory chain in cells over-expressing Bcl-$x_L$ was more sensitive to antimycin A, cellular respiration was measured by oximetry. Briefly, TABX2S cells (over-expressing Bcl-$x_L$) and control cells (TAMH.neo) were suspended in air-equilibrated complete medium at a density of 3 million cells per milliliter and placed in a thermostatted electrode chamber at 37° C. The cells were treated with 1 µg/ml antimycin A. Polarographic measurements were made with a Clark-type oxygen electrode with continuous recording. Both cell types showed similar reductions in oxygen consumption. At higher concentrations of antimycin A, oxygen consumption was almost completely inhibited in TAMH.neo control cells, while TABX2S cells maintained about 20 percent of basal oxygen consumption. Thus, the sensitivity of cells over-expressing Bcl-$x_L$ to antimycin A was not a result of heightened effects on ATP levels, ROS generation or cell respiration.

The effect of antimycin A on mitochondrial function was further evaluated with the mitochondrial dye, JC-1 (5,5',6,6'-tetrachloro-1,1',3,3'-tetraethylbenzimid-azolcarbocyanine iodide) (Molecular Probes, Eugene, Oreg.), a lipophilic, cationic carbocyanine dye, which has a fluorescence emission at 520 nm (green). JC-1 normally exists in solution as a monomer emitting a green fluorescence. When JC-1 assumes a dimeric configuration (J-aggregate) in a reaction driven by $\Delta\Psi_m$, it emits a red fluorescence (Reers et al., *Biochem.* 30:4480–86 (1991)). The use of JC-1 allows simultaneous analysis of mitochondrial volume (green fluorescence) and $\Delta\Psi_m$ (red fluorescence). (See Mancini et al., *J. Cell. Biol.* 138:449–69 (1997).)

Briefly, at 15 and 30 minutes, $5 \times 10^5$ cells were washed, trypsinized and resuspended in 1 ml of growth media. Each sample was stained with 10 µg/ml of JC-1 prepared in DMSO. After 10 minutes of incubation at 37° C., cells were transferred to ice and analysis was performed using a FACScan flow cytometer (Becton Dickinson). The excitation wavelength was 488 nm whereas measurement was performed at 520 and 585 nm for green and red fluorescence, respectively. Green and red fluorescence were measured on FL1 and FL2 channels, respectively. A minimum of 10,000 cells per sample were analyzed. Comparisons were made based on the results of at least three experiments.

There was a clear increase in JC-1 green fluorescence (mitochondrial volume), accompanied by a decline in JC-1 red fluorescence (mitochondrial transmembrane potential) in TABX2S cells one hour after antimycin A treatment. In contrast, JC-1 green and red fluorescence remained relatively unchanged in TABX1A cells. It should be noted that in the control cells (DMSO vehicle-treated cells), neither JC-1 green nor red fluorescence changed after one hour. When earlier time points were examined in TABX2S cells, there was already a significant increase (shift to right) in JC-1 green fluorescence as early as 15 minutes after addition of antimycin A, whereas JC-1 red fluorescence showed little change at this time. This finding suggests that the change of mitochondrial volume precedes that of $\Delta\Psi_m$.

The ultrastructural characteristics of TABX2S and TABX1A cells were further studied by electron microscopy. Briefly, cells were fixed in half strength Karnovsky's fixative and post-fixed in 1% collidine buffered osmium tetroxide. After dehydration, cells were embedded in Epon 812. Ultrathin sections were stained using saturated aqueous uranyl acetate and lead tartrate and examined using a JEOL 100 SX transmission electron microscope operating at 80 kV. At two hours after exposure to antimycin A, TABX2S cells had become shrunken and displayed chromatin condensation and margination in the nuclei. The mitochondrial morphology was normal in antimycin A-treated TABX1A (control) cells. These data confirm the apoptotic nature of the cell death. The mitochondria were markedly swollen with widening of the cristae, consistent with the increased JC-1 green fluorescence observed previously in this example. JC-1 staining, however, was found to be more sensitive in detecting mitochondrial changes because mitochondrial swelling was not apparent at 30 minutes or one hour when assayed by electron microscopy.

Mitochondrial PT is caused by opening of a large conductance channel in the inner mitochondrial membrane. Opening of a large conductance channel allows free distribution of solutes of less than 1,500 Da and results in dissipation of the proton gradient and osmotic swelling of mitochondria due to the higher solute concentration in the matrix. In isolated mitochondria, the colloid osmotic swelling associated with PT pore opening can be followed by measuring the optical density change at 540 nm (Kantrow et al., *Biochem. Biophy. Res. Comm.* 232:669–71 (1997)). Because antimycin A-treated TABX2S cells demonstrated increased JC-1 green fluorescence by flow cytometry and mitochondrial swelling by electron microscopy, which suggested the occurrence of PT, the effect of antimycin A in PT induction of isolated mitochondria was tested.

Briefly, mitochondria were isolated from TABX2S cultured cells by a modification of the procedure of Maltese et al. (*J. Biol. Chem.* 260:11524–29 (1985)). Typically, 0.5 to 1×10$^8$ cells were harvested and washed once with homogenization buffer (250 mM sucrose, 10 mM Tris-HCl, 1 mM EDTA and 1 mg/ml BSA, (pH 7.4)). The cell suspension was exposed to nitrogen at 250 psi for 30 minutes in a "cell disruption bomb" (Parr, Moline, Ill.) or homogenized in a Dounce homogenizer with a loose-fitting pestle until >90% of cells were broken. The homogenate was centrifuged at 800×g for 10 minutes. The supernatant was removed and centrifuged at 10,000×g for 10 minutes at 4° C. The pellet was resuspended and again centrifuged at 10,000×g for 10 minutes. The mitochondrial pellet thus obtained was resuspended and adjusted to 0.5 mg protein/ml in an isotonic buffer consisting of 100 mM KCl, 75 mM mannitol, 25 mM sucrose, 5 mM Tris-phosphate, 10 mM Tris-HCl (pH 7.4), 0.05 mM EDTA and 5 mM succinate. For light scattering studies (e.g., for measurement of PT), the mitochondrial suspension was placed in a quartz cuvette, and continuous measurements of light absorption at 540 nm were obtained using a PerkinElmer Lambda 2 spectrophotometer.

Antimycin A added directly to the purified mitochondrial preparation at a concentration of 2 µg/ml caused PT, which was detected by a rapidly occurring drop in absorbance at 540 nm in mitochondria prepared from TABX2S cells. A rapid fall in light absorbance is characteristic of large amplitude swelling. In contrast, mitochondria from TABX1A cells did not exhibit similar permeability changes and swelling, even at much higher concentrations of antimycin A. The addition of 100 mM CaCl$_2$ resulted in mitochondrial swelling of both TABX2S and TABX1A mitochondria. In contrast to these results with antimycin A, Bcl-x$_L$-expressing mitochondria were moderately resistant to calcium-triggered mitochondrial swelling.

The effects of antimycin A on mitochondrial membrane potential, using $\Delta\Psi_m$-sensitive JC-1 probe were also tested. Isolated mitochondria were loaded with JC-1 prior to treatment, and mitochondrial labeling was determined using FACS. Relative to either initial mitochondrial red fluorescent staining or the lowered fluorescent intensity of mitochondria treated with an uncoupler, CCCP, antimycin A caused a much greater decrease in $\Delta\Psi_m$ mitochondria having high levels of Bcl-x$_L$ (TABX2S) than control mitochondria (TABX1A). Antimycin A-treated mitochondria with high levels of Bcl-2 had lower levels of JC-1 staining than parallel samples treated with CCCP. Uncoupled mitochondria still retain a significant Donnan potential because of trapped anionic species and it is likely that antimycin-induced PT and/or swelling of mitochondria led to a further reduction of this residual potential. Mitochondria from TAMH.neo cells had an intermediate response to antimycin A.

In summary, examination of mitochondrial characteristics of transfected cells over-expressing Bcl-x$_L$ in response to antimycin A demonstrated that ATP depletion and increased ROS production, which are parameters of complex III inhibition, did not correlate with cell death. Rather, antimycin A induced mitochondrial swelling in cells over-expressing Bcl-x$_L$ cells, as demonstrated by the flow cytometry and electron microscopy data discussed above. In addition, the findings that isolated mitochondria over-expressing Bcl-x$_L$ undergo rapid swelling associated with PT, while control mitochondria are completely resistant, clearly demonstrated the local effect of Bcl-x$_L$ conferring antimycin sensitivity on mitochondria. Thus, antimycin A causes preferential cell death by a mechanism independent of its mitochondrial complex III inhibition.

EXAMPLE 3

This example demonstrates that antimycin A-induced cell death is caspase independent. Bcl-2-like proteins can suppress apoptosis through direct and indirect effects on the cytosolic caspase-activating apoptosome complex (caspase-9, APAF-1 and cytochrome c) or by maintaining mitochondrial membrane integrity and osmotic homeostasis (Cosulich et al., *Curr Biol.* 9:147–50 (1999)). Thus, antimycin A could initiate apoptosis in Bcl-x$_L$-over-expressing cells by inducing Bcl-x$_L$ to promote, rather than oppose caspase activation, possibly by altering interactions with APAF-1 (Pan et al., *J. Biol. Chem.* 273:5841–5 (1998); Hu et al., *Proc Nat. Acad. Sci USA.* 95:4386–91 (1998)).

TABX2S and TABX1A cells were exposed to the broad spectrum caspase inhibitor, benzyloxycarbonyl-Val-Ala-Asp-fluoromethyl ketone (zVAD-fmk). Antimycin A-induced death of TABX2S cells was found to be caspase-independent, as shown by the inability of zVAD-fmk to rescue such cells from cell death. This result indicates that the pro-apoptotic activity of the antimycin A does not require caspase activity.

EXAMPLE 4

In this example the ability of antimycin A to prevent pore formation by Bcl-$x_L$ was tested using a rhodamine 123 ("Rh-123") retention assay (Petit et al., *Eur. J. Biochem.* 194:389–97 (1990); Imberti et al., *J. Pharmacol. Exp. Ther.* 265:392–400 (1993), each incorporated herein by reference). Rh-123 is a cationic lipid-soluble fluorescent dye that accumulates in mitochondria in proportion to the mitochondrial membrane potential. Mitochondria were isolated from TABX2S cells (over-expressing Bcl-$x_L$) and from control cells, prepared as described in Example 2. The isolated mitochondria were loaded with Rh-123 by incubating with 10 µM Rh-123 for 30 minutes, washed and resuspended in buffer. Five minutes after adding antimycin A, or a control diluent, the level of Rh-123 retained by the mitochondria was determined by flow cytometry. Less than 40% of Rh-123 was retained in antimycin A-treated TABX2S mitochondria, compared with greater than 80% retained in control mitochondria. These results indicate that antimycin A induces membrane depolarization, with rapid kinetics, in mitochondria from TABX2S cells, but not in control mitochondria.

EXAMPLE 5

To probe a potential interaction between antimycin A and Bcl-$x_L$, docking analysis was performed using the crystallographic structure of the Bcl-$x_L$ protein and antimycin A coordinates from the NMR structure (Muchmore et al., *Nature* 381:335–41 (1996); Sattler et al., *Science* 275: 983–86 (1997)) and the Available Chemicals Directory (Molecular Design, Ltd., San Leandro, Calif.). The program suite, DOCK (Kuntz, *Science* 257:1078–82 (1992)), was used to determine if there is a compatible site on Bcl-$x_L$ for binding of antimycin A and, if so, and an optimal binding configuration. The DOCK program systematically moves the molecular structure of antimycin A along the surface of the Bcl-$x_L$ structure and searches for a potential binding site based on shape complementarity, electrostatic interaction, hydrogen bond formation and other chemical energies. An optimal binding site was identified in the Bcl-$x_L$ structure. Antimycin A was predicted to bind in an extended conformation to the hydrophobic pocket of Bcl-$x_L$ formed by three conserved domains in the Bcl-2 family, BH1, BH2, and BH3. This binding site overlapped with the dimerization interface for Bak BH3 peptide and Bcl-$x_L$ previously determined by NMR spectroscopy (Sattler et al., *Science* 275: 983–86 (1997)).

EXAMPLE 6

Based on the computer modeling prediction that antimycin A could directly bind to the hydrophobic pocket of Bcl-$x_L$, fluorescence spectroscopy was used to detect such a direct interaction. Antimycin $A_3$ exhibits fluorescence at 428 nm. The binding of antimycin $A_3$ to protein causes an increase in that fluorescence.

In this assay, 0 to 5 µM antimycin $A_3$ (Sigma Chemical Co., St. Louis, Mo.) was added to a physiological buffer (50 mM Tris-HCl pH 8.0, 0.2 M NaCl, 2 mM EDTA, 0.5% v/v glycerol) containing recombinant Bcl-$x_L$ protein under conditions that permitted antimycin $A_3$ to bind to the BH3-binding domain of Bcl-$x_L$ (22.5° C. on a Hitachi F-2500 fluorescence spectrofluorimeter equipped with a thermostatted cell holder). Bovine serum albumin (BSA), which is known to bind antimycin A, and lysozyme were used as positive and negative controls, respectively. The excitation wavelength was 335 nm, and the maximum emission wavelength for antimycin $A_3$ was 428 nm with a slit width of 10 mm. The samples were mixed in a quartz cuvette and check for inner filter effect over the range of antimycin $A_3$ for this study. Blanks containing antimycin $A_3$ at the same concentration as the experimental samples were used as controls in all measurements and necessary background corrections were made.

Recombinant human Bcl-2$\Delta$C22 and mouse Bcl-$x_L\Delta$C20 fused with poly-His at the N-terminus were chromatographically purified to homogeneity. The concentrations of antimycin $A_3$ and stock solutions of recombinant proteins were quantitated using an extinction coefficient of 7.24/mM/cm at 320 nm and by Bradford assay, respectively. The stoichiometric ratio of antimycin $A_3$ and Bcl-2 producing the maximal change in antimycin $A_3$ fluorescence was determined with incremental addition of antimycin $A_3$ to a 1.98 µM solution of recombinant Bcl-2 in a volume of 2.1 milliliters. The change in volume resulting from the addition of antimycin $A_3$ was less than 5%. For peptide displacement experiments, a solution of 2 µM antimycin $A_3$ and 3 µM Bcl-2 was allowed to reach binding equilibrium at 4° C. prior to fluorescence measurements. Native peptide corresponding to the BH3 domain of Bak (72-GQVGRQLAI-IGDDINR-87 (SEQ ID NO:1); synthesized at Colorado State University) or a mutant peptide with a single amino acid change (Leu78Ala-BH3) was added to the solution and the fluorescence measurements were repeated.

The fluorescence of the solution containing recombinant Bcl-$x_L$ and antimycin $A_3$ was increased above the fluorescence of antimycin $A_3$ alone, indicating that binding had occurred. The fluorescence intensity of antimycin $A_3$ also increased in the presence of BSA (the positive control), but not in the presence of lysozyme (negative control). The intrinsic fluorescence at 428 nm of antimycin $A_3$ increases by as much as 18% in the presence of Bcl-2 protein. The maximum change in fluorescence intensity of antimycin $A_3$ was observed at a molar stoichiometric ratio of antimycin $A_3$ to Bcl-2 of 1:1, as determined from a Job plot.

The BH3 peptide is also known to bind to the hydrophobic pocket of Bcl-$x_L$ and Bcl-2. To determine if the site of antimycin $A_3$ interaction was the hydrophobic pocket of Bcl-2, a competitive binding assay was used to determined if the 16 residue Bak BH3 peptide could displace antimycin $A_3$ bound to Bcl-2. The Bak BH3 peptide binds to the hydrophobic pocket of Bcl-2. The relative concentrations of antimycin $A_3$ and Bcl-2 were adjusted to maximize formation of the antimycin $A_3$:Bcl-2 complex, as indicated by the fluorescence shift of antimycin $A_3$. BH3 peptide was then added to the preformed antimycin $A_3$:Bcl-2 complex, as described above. The fluorescence intensity of antimycin $A_3$ was inversely related to the concentration of BH3 peptide added. At a molar excess of BH3 peptide, antimycin $A_3$ fluorescence coincided with that for solutions of free antimycin $A_3$ (without Bcl-2), indicating the displacement of antimycin $A_3$ from Bcl-2. No overlapping fluorescence was observed from either the BH3 peptide or Bcl-2:BH3 peptide complex, and BH3 peptide alone did not affect antimycin $A_3$ fluorescence. BH3 peptide displaced antimycin $A_3$ from Bcl-2 polypeptide with an approximate Michaelis constant of 2.5 µM.

The ability of the mutant Bak BH3 peptide, Leu78Ala-BH3 (L78A-BH3), to displace antimycin $A_3$ bound to Bcl-2 polypeptide was also tested. The affinity of L78A-BH3 peptide for the Bcl-$x_L$ hydrophobic pocket is diminished by two orders of magnitude compared to native Bak BH3 peptide. The L78A-BH3 peptide showed significantly reduced ability to displace antimycin $A_3$ from Bcl-2. Equivalent displacement of antimycin $A_3$ occurred at a forty fold higher concentration of L78A-BH3 peptide than that required for the native Bak BH3 peptide, which demonstrated the specificity of antimycin $A_3$-binding to the hydrophobic pocket of Bcl-2. The displacement of antimycin $A_3$ from Bcl-$x_L$ similarly required much higher concentrations of the L78A BH3 peptide. These results are consistent with the docking model in which antimycin $A_3$ is predicted to bind to Bcl-$x_L$ at the same binding site as the BH3 peptide the hydrophobic pocket.

EXAMPLE 7

The effects of antimycin A in TABX2S cells are similar to the reported mitochondrial and pro-apoptotic effects of peptides derived from the BH3 domain of Bax-like proteins (Chittenden et al., *EMBO J.* 14:5589–96 (1995); Cosulich et al., *Curr Biol.* 7:913–20 (1997); Holinger et al., *J. Biol. Chem.* 274:13298–304 (1999)). This observation led us to test if Bak-derived BH3 peptide also selectively depolarized mitochondria from TABX2S cells (over-expressing Bcl-$x_L$).

In this experiment, the synthetic-prepared 16-residue Bak BH3 peptide (Example 6) was added to mitochondria from TABX2S cells (over-expressing Bcl-$x_L$) and to control cells. The addition of the Bak BH3 peptide at 3.5 µM induced similar Rh123 dye leakage by TABX2S mitochondria as that produced by antimycin A. Mitochondria from TABX1A cells were minimally affected by the same concentration of BH3 peptide, or by antimycin A. Thus, antimycin A acts like Bak BH3 peptide in inducing membrane depolarization. Although high levels of Bcl-$x_L$ maintain mitochondrial integrity in intact cells or isolated organelles exposed to a wide range of stressors, the addition of antimycin A or Bak BH3 peptide overcomes this resistance to depolarization. In contrast, the control cells, which express Bcl-$x_L$ at physiological levels, were resistant to BH3 peptide-induced membrane depolarization.

This dichotomy can perhaps best be explained by the specific interaction of pro-apoptotic BH3 peptides with the hydrophobic groove in the Bcl-$x_L$ structure (Sattler et al. *Science* 275:983–86 (1997)). Reduced levels of Bcl-$x_L$ result in a lower number of binding sites for BH3 peptides and resistance to BH3-mediated effects. A similar mechanism may explain the specific effects of antimycin A on Bcl-$x_L$-expressing mitochondria These results suggest that antimycin A acts as a molecular mimic of endogenous pro-apoptotic proteins. Low expression of Bcl-$x_L$ reduces the mitochondrial toxicity of both antimycin A and BH3 peptide

EXAMPLE 8

In this example the ability of antimycin A to prevent pore formation by Bcl-$x_L$ was tested. The Bcl-$x_L$ protein has reversible pore-forming activity. The hydrophobic pocket is part of the cytoplasmic portion of Bcl-$x_L$ protein tertiary structure. Recombinant human Bcl-$x_L$ lacking the C-terminal twenty membrane anchor sequence, Bcl-$x_L\Delta C20$, forms pores in large unilamellar vesicles. A reporter, calcein, can leak out of the vesicles through these pores. If antimycin A affects Bcl-$x_L\Delta C20$ pore formation, the leakage of calcein will change, as can be measured by a change in fluorescence.

Large unilamellar vesicles composed of 60% dioleoylphosphatidylcholine and 40% oleoylphosphatidylglycerol were prepared by the extrusion method of Mayer et al. (*Biochim. Biophys. Acta* 858:161–68 (1986), incorporated herein by reference in its entirety). Briefly, a dry film of lipid was resuspended in an aqueous solution containing 40 mM calcein (Molecular Probes, Eugene, Oreg.), 25 mM KCl and 10 mM HEPES (pH 7.0). After 5 freeze-thaw cycles, the lipidic solution was extruded through 2 Nucleopore filters, 0.1 µm pore diameter. Nonencapsulated material was removed from the vesicles using a SEPHADEX G-50 column (Pharmacia, Uppsala, Sweden), with 10 mM HEPES (pH 7.0), 100 mM NaCl, as the elution buffer. The size of the vesicle suspension was measured by a Coulter N4 Plus-Sizer to confirm that the mean diameter of the vesicle sample was close to the expected size (100 nm). The osmolalities of all solutions were measured in a cryoscopic osmometer (Wescor Inc., Logan, Utah) and adjusted to 0.21 Osmol/kg by the addition of sodium chloride, as necessary. Lipid concentration was measured as described previously (Stewart, *Anal. Biochem.* 104:10–14 (1989), which incorporated herein by reference in its entirety).

Calcein leakage was determined by adding 2–4 µg of purified Bcl-$x_L\Delta C20$ (5 µg/ml, 161 nM) to a solution of 100 mM NaCl, 10 mM HEPES (pH 5.0) containing the large unilamellar vesicles (50 µM final lipid concentration) described above. Changes in the fluorescence intensity were measured in an Aminco-SLM spectrofluorimeter. BH3 peptides and antimycin derivatives were incubated with Bcl-$x_L$ for 5 minutes prior to addition to the liposome suspension. Assays were performed at 37° C. in a thermostatted cuvette with constant stirring. Excitation and emission wavelengths for calcein were 495 nm and 520 nm, respectively, at a slit width of 4 nm. The 100% fluorescence level for leakage was obtained by detergent lysis (0.1% TRITON X-100) of the vesicles containing entrapped calcein.

In vesicles preloaded with calcein, about 40% of the reporter leaks from the vesicles within about 3 minutes of Bcl-$x_L\Delta C20$ addition. Leakage of calcein was inhibited in a dose-dependent fashion by antimycin A. At a concentration of 12 µM, antimycin A completely blocked Bcl-$x_L$ pore-forming activity.

The ability of the Bak BH3 peptide to induce leakage of calcein was also tested. Native BH3 peptide inhibited Bcl-$x_L$-induced calcein efflux from synthetic liposomes, with 50% inhibition at about a 20:1 molar ratio of Bak BH3 peptide:Bcl-$x_L$ protein. This inhibition is equivalent to the approximately 20:1 molar ratio of antimycinA:Bcl-$x_L$ that is required to achieve a 50% inhibition of calcein leakage. In contrast, the mutant L78A-BH3 peptide has a minimal effect on Bcl-$x_L$-induced pore formation even at a 100-fold molar excess. Thus, antimycin A is capable of blocking the ability of Bcl-$x_L$ to act as a membrane pore.

EXAMPLE 9

Studies of cellular respiration, ATP levels and reactive oxygen species in antimycin A-treated cell lines strongly suggested that the observed differences in cell viability could not be explained by the known effects of antimycin A on mitochondrial electron transfer or oxidative phosphorylation. To definitively address which activities of antimycin A are involved in the selective cell death of cell overexpressing Bcl-$x_L$, the structure-activity relationship for antimycin $A_3$ as an inhibitor of Bcl-$x_L$ pore activity was determined.

In this example, two derivatives of antimycin $A_3$ were prepared, antimycin $A_3$ methyl ether (2-methoxy ether antimycin $A_3$) and phenacyl ether antimycin $A_3$. The structure of antimycin $A_3$ was shown above (formula (I), where $R_1$ is a butyl group). (See also van Tamelen et al, *J. Am. Chem. Soc.* 83:1639 (1961)). Antimycin $A_3$ methyl ether has the following formula (VI) and an absolute configuration of [2R, 3R, 4S, 7S, 8R]:

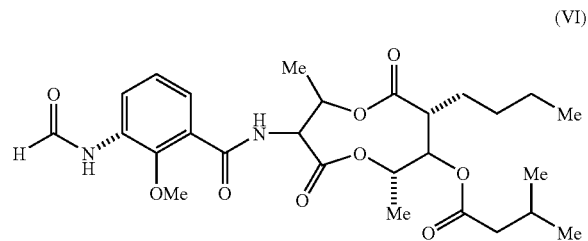

(VI)

Antimycin $A_3$ methyl ether is prepared directly from antimycin $A_3$ as follows: Briefly, antimycin $A_3$ (14.0 mg) was dissolved in ethyl ether and a stream of diazomethane was passed through the reaction mixture until the yellow color persisted. The reaction mixture was treated with acetic acid until it became colorless. The mixture was reduced to dryness under reduced pressure and chromatographed on silica gel to yield 14.3 mg of antimycin $A_3$ methyl ether. The resulting product was characterized by NMR, infrared spectroscopy and mass spectroscopy.

The phenacyl ether derivative of antimycin $A_3$ was prepared as follows: A solution of antimycin $A_3$ (5.7 mg, 10.95 mmol) in dry acetonitrile was treated with phenacyl bromide (4.4 mg, 21.9 mmol) and powdered potassium carbonate (6.0 mg, 43.8 mmol). The mixture was allowed to stir at room temperature for 18 hours. The reaction mixture was applied directly to a silica gel chromatography column. The product was eluted with 20% ethyl acetate/hexane to yield 5.4 mg (78%) of the product as a colorless oil. The resulting product was characterized by NMR, infrared spectroscopy and mass spectroscopy.

EXAMPLE 10

The antimycin $A_3$ methyl ether derivative prepared in Example 9 was studied to determine its affect on the apoptotic pathway in cells over-expressing BCl-$x_L$. The methyl ether derivative was previously shown to be inactive as an inhibitor of cytochrome $bc_1$. (See, e.g., Miyoshi et al., *Biochim Biophys Acta* 1229:149–54 (1995); Takotake et al., *Biochim Biophys Acta* 1185:271–78 (1994).) The methyl ether also has a negligible effect on cellular $O_2$ consumption compared to the original antimycin $A_3$ compound. TABX2S (over-expressing Bcl-$x_L$), TAMH.neo (control) and TABX1A (antisense) cell lines were treated with 2-methoxy antimycin $A_3$. These cell lines exhibited a pattern of preferential cytotoxicity for cells over-expressing Bcl-$x_L$, but not for control cells. This pattern was similar to that to antimycin $A_3$ treatment of these cell lines, indicating that the effect of this antimycin derivative on cellular respiration was separable from that on apoptosis.

To confirm this data, assays were also performed with mitochondrial fractions from each cell line using the mitochondrial probe JC-1. Mitochondria from cells over-expressing Bcl-$x_L$ (TABX2S cells) were strongly depolarized after addition of the 2-methoxy derivative at a concentration of 2 μg/ml. As observed for the parent compound, antimycin $A_3$, mitochondria with normal levels of Bcl-$x_L$ expression were not affected by the 2-methoxy analog.

Finally, the 2-methoxy antimycin $A_3$ derivative was shown to bind recombinant Bcl-2. The 2-methoxy antimycin $A_3$ derivative is non-fluorescent due to the additional electrophilic substituent on the benzene ring. Thus, binding of 2-methoxy antimycin $A_3$ to the Bcl-2 protein can be measured in a competitive binding assay by monitoring fluorescence from antimycin $A_3$. For these experiments, antimycin $A_3$ (2 μM) and either 2-methoxy ether antimycin $A_3$ or phenacyl ether antimycin $A_3$ (2 μM) were added simultaneously to Bcl-2 polypeptide (3 μM) and allowed to equilibrate for 7.5 minutes at 22.5° C. before measuring the fluorescence intensity of antimycin $A_3$. The fluorescence of a prebound antimycin $A_3$-recombinant Bcl-2 complex decreased exponentially with the addition of 2-methoxy antimycin $A_3$, indicating competition for the antimycin $A_3$ binding site on Bcl-2. As an additional control for binding specificity, the effect of the phenacyl ether derivative of antimycin $A_3$ was also tested. Although of similar hydrophobicity, the phenacyl ether derivative did not displace antimycin $A_3$ from Bcl-2. These results strongly suggest that the cellular and mitochondrial sensitivity to antimycin $A_3$ in Bcl-$x_L$ expressing cell lines results from direct binding of antimycin $A_3$ to Bcl-$x_L$ protein. Furthermore, the 2-methoxy ether antimycin $A_3$ derivative inhibited Bcl-$x_L$ pore formation in a liposome permeability assay almost as well as antimycin $A_3$.

The results demonstrate that the antimycins have two structurally distinguishable protein-binding activities, one for binding to cytochrome $bc_1$, and the other for binding to Bcl-2 family member proteins, and that these activities are separable.

EXAMPLE 11

The total synthesis of antimycin $A_3$ is carried out essentially as described by Shimano for the related dilactones UK-2A and UK-3A (Shimano, *Tetrahedron* 54:12745–74 1998). Briefly, antimycin $A_3$ is composed of three structural units: an N-formyl-3-aminosalicylic acid, L-threonine and 2-butyl-3,4-dihydroxypentanoic acid. Of the three structural components, N-formyl-3-aminosalicylic acid and L-threonine are commercially available. The dihydroxy pentanoic acid is prepared in a four-step reaction sequence starting with caproyl chloride. Referring to FIG. 1, caproyl chloride is reacted with the Evans valine-derived oxazolidinone, (R)-4-isopropyloxazolidin-2-one, and n-butylLi (Step a). The resulting adduct (2) is reacted by aldol condensation with a chiral aldehyde derived from (S)-(–)-lactic acid (3) in the presence of dibutyl-BOTf and triethylamine (Step b). The 4-hydroxyl group of the resulting adduct (4) is protected as a t-butyldimethylsilyl ether (using TBS chloride and DIEA), followed by peroxide-mediated hydrolysis (using hydrogen peroxide and lithium hydroxide) of the chiral auxiliary to yield the differentially protected dihydroxy pentanoic acid (5) (Steps c and d). Differential protection of the two secondary alcohols allows for the incorporation of various carboxylic acids at the 3 position of the lactone. The carboxylic acid is coupled to N-FMOC-L-threonine benzyl ester with BOP-chloride and DMAP (Step e). Removal of the two benzyl protecting groups with $H_2$ and Pd/O will yield the dilactone seco-acid (6) (Step f). Lactonization occurs using a BOP-Cl mediated ester-forming reaction with DMAP (Step g). Diethylamine is used to remove the FMOC protecting group to yield the dilactone (7) (Step h). N-formyl-3-amine salicylic acid is coupled to the dilactone using standard carbodiimide chemistry (Step i). In particular, the dilactone is combined with N-formyl-3-aminosalicylic acid using EDCl and HOBT, followed by treatment with TBAF. The final elaboration of the derivatized antimycin A3 structure is accomplished by fluoride-mediated removal of the silyl protecting group and coupling of the desired acid chloride (e.g., isovaleryl chloride and DIEA) (Steps j and k).

EXAMPLE 12

To prepare derivatives of antimycin $A_3$ that are modified in the isovalerate moiety (i.e., $R_2$) of the dilactone, the total synthesis of antimycin $A_3$ (as described in Example 11) is conducted with the following modifications: After dilactonization, the isovaleryl chloride is substituted by another acyl chloride, such as acetyl chloride, butyryl chloride, and the like.

EXAMPLE 13

To prepare derivatives of antimycin $A_3$ in which the isovalerate moiety (i.e., $R_2$) of the dilactone is replaced with a hydroxyl group, the total synthesis of antimycin $A_3$ (as described in Example 11) is conducted up to the last step, at which step the addition of the acyl chloride is omitted.

EXAMPLE 14

To prepare derivatives of antimycin $A_3$ in which the butyl group (i.e., $R_1$) on the dilactone is substituted with another R group, the total synthesis of antimycin $A_3$ (as described in Example 11) is conducted with the following modifications: The caproyl chloride of step 1 is substituted with another acyl chloride, such as propionyl chloride or another linear or branched acyl chloride.

EXAMPLE 15

To prepare derivatives of antimycin $A_3$ in which the 8-methyl group (i.e., $R_6$) on the dilactone is substituted with another R group, the total synthesis of antimycin $A_3$ (as described in Example 11) is conducted with the following modifications: The N-FMOC-L-threonine benzyl ester of step 6 is substituted with an N-FMOC-L-serine benzyl ester.

EXAMPLE 16

To prepare derivatives of antimycin $A_3$ in which the 8-methyl group (i.e., $R_6$) on the dilactone is substituted with a different $R(C_2-C_6)$ group, the total synthesis of antimycin $A_3$ (as described in Example 11) is conducted with the following modifications: The N-FMOC-L-threonine benzyl ester of step 6 is substituted with an N-FMOC-α-amino-β-hydroxy ($C_2-C_6$) carboxylic acid benzyl ester (e.g., for $C_2$: 2-amino-3-hydroxy pentanoic acid benzyl ester).

EXAMPLE 17

To prepare a derivative of antimycin $A_3$ in which the butyl and isovalerate groups (i.e., $R_1$ and $R_2$) are replace with a benzene ring, the total synthesis of antimycin $A_3$ (as described in Example 11) is modified as follows: N-FMOC L-threonine methyl ester is coupled with the tert-butyl-dimethylsilyl ether of 2-hydroxymethyl benzoic acid in the presence of EDCI and disopropylethylamine. The resulting ester is treated with diethyl amine to liberate the alpha-amino group. The N-formyl-amino salicylic acid is attached using standard carbodiimide chemistry. The threonine methyl ester and the silyl group are removed by treatment with aqueous base. The resulting hydroxyacid is lactonized using carbodiimide chemistry.

The resulting compound has the following formula VII:

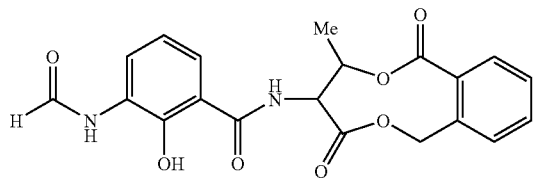

EXAMPLE 18

To prepare derivatives of antimycin $A_3$ that are modified in the salicylic acid moiety, the total synthesis of antimycin $A_3$ is carried out described in Example 11 through the lactonization step. Following lactonization, the N-formyl-3-amine salicylic acid is replaced with one of the following compounds to form an antimycin $A_3$ derivative:

| Antimycin $A_3$ Derivative | Compound |
| --- | --- |
| 3-methylbutanoic acid 8-butyl-3-[[3-amino-2-hydroxybenzoyl]amino]-2,6-dimethyl-4,9-dioxo-1,5-dioxonan-7-yl ester | amino salicylic acid (2-hydroxy-3-aminobenzoic acid) |
| 3-methylbutanoic acid 8-butyl-3-[[3-(acetylamino)-2-hydroxybenzoyl]amino]-2,6-dimethyl-4,9-dioxo-1,5-dioxonan-7-yl ester | N-acetyl-3-amine salicylic acid |
| 3-methylbutanoic acid 8-butyl-3-[[3-(propionylamino)-2-hydroxybenzoyl]amino]-2,6-dimethyl-4,9-dioxo-1,5-dioxonan-7-yl ester | N-propionyl-3-amine salicylic acid |
| 3-methylbutanoic acid 8-butyl-3-[[2-hydroxybenzoyl]amino]-2,6-dimethyl-4,9-dioxo-1,5-dioxonan-7-yl ester | salicylic acid |

Although the foregoing invention has been described in some detail by way of illustration and example for purposes of clarity of understanding, it will be obvious that certain changes and modifications may be practiced within the scope of the appended claims. The scope of the invention should, therefore, be determined not with reference to the above description, but instead should be determined with reference to the appended claims along with their full scope of equivalents. All publications and patent documents cited in this application are incorporated by reference in their entirety for all purposes to the same extent as if each individual publication or patent document were so individually denoted.

What is claimed is:

1. An apoptotic composition that induces apoptosis by binding to a Bcl-2 family member protein and preferentially inducing apoptosis in a cell that over-expresses the Bcl-2 family member protein, the composition having the following formula II,

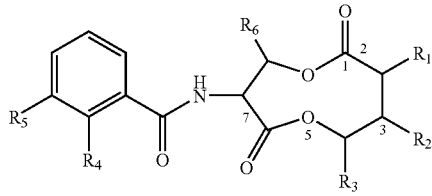

having an absolute configuration of [2R, 3R, 4S, 7S, 8R], and wherein $R_1$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group;

$R_2$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group;

$R_3$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group;

$R_4$ is hydrogen, a $C_1$–$C_8$ linear or branched alkane, a $C_1$–$C_8$ hydroxyalkane, or a substituted alkyl group;

$R_5$ is hydrogen, a $C_1$–$C_8$ linear or branched alkane, hydroxyl, a $C_1$–$C_8$ hydroxyalkane, amino, a $C_3$–$C_8$ di- or tri-alkylamine, a $C_1$–$C_8$ carboxylic acid, a $C_2$–$C_8$ amide, or a substituted alkyl group; and $R_6$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group.

2. The composition of claim 1, further comprising a pharmaceutically acceptable carrier.

3. The composition of claim 1 for use in treating cancer in a subject in need thereof.

4. A method for treating a subject having cancer comprising administering to the subject a therapeutically effective amount of a composition, wherein the composition comprises an antimycin of the following formula, and having an absolute configuration of [2R, 3R, 4S, 7S, 8R]:

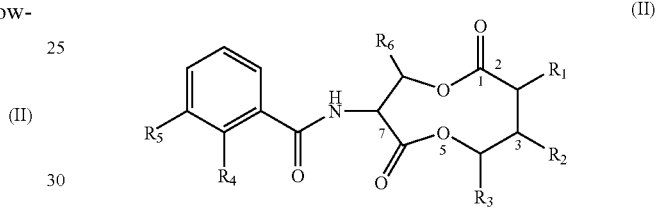

wherein $R_1$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group;

$R_2$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group;

$R_3$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group;

$R_4$ is hydrogen a $C_1$–$C_8$ linear or branched alkane, hydroxyl, a $C_1$–$C_8$ hydroxyalkane or a substituted alkyl group;

$R_5$ is hydrogen, a $C_1$–$C_8$ linear or branched alkane, hydroxyl, a $C_1$–$C_8$ hydroxyalkane, amino, a $C_1$–$C_8$ di- or tri-alkylamine, a $C_1$–$C_8$ amide, a $C_1$–$C_8$ carboxylic acid, or a substituted alkyl group; and $R_6$ is hydrogen, a $C_1$–$C_8$ linear or branched alkane, hydroxyl, a $C_1$–$C_8$ hydroxyalkane, amino, a $C_1$–$C_8$ di- or tri-amine, a $C_1$–$C_8$ amide, a $C_1$–$C_8$ carboxylic acid, or a substituted alkyl group.

5. The method of claim 4, wherein the antimycin derivative is 2-methoxy ether antimycin A or $A_3$.

6. The method of claim 4, wherein the subject is human.

7. The method of claim 4, further comprising administering a pharmaceutical carrier.

8. The method of claim 4, wherein the administration is intravenous, subcutaneous, intramuscular, intradermal, transdermal, intrathecal, intracerebral, intraperitoneal, epidural or oral.

* * * * *

SEQUENCE LISTING

<160> NUMBER OF SEQ ID NOS: 1

<210> SEQ ID NO 1
<211> LENGTH: 16
<212> TYPE: PRT
<213> ORGANISM: Artificial Sequence
<220> FEATURE:
<223> OTHER INFORMATION: Description of Artificial Sequence: BH3 domain
      of Bak

<400> SEQUENCE: 1

Gly Gln Val Gly Arg Gln Leu Ala Ile Ile Gly Asp Asp Ile Asn Arg
1               5                   10                  15